US011041838B2

(12) United States Patent
Rogers et al.

(10) Patent No.: US 11,041,838 B2
(45) Date of Patent: Jun. 22, 2021

(54) GAS SENSORS INCLUDING MICROHOTPLATES WITH RESISTIVE HEATERS, AND RELATED METHODS

(71) Applicant: Nevada Nanotech Systems Inc., Sparks, NV (US)

(72) Inventors: Ben Rogers, Reno, NV (US); Christopher J. Dudley, Reno, NV (US); Dean A. Hopkins, Reno, NV (US); Emil J. Geiger, Reno, NV (US)

(73) Assignee: Nevada Nanotech Systems Inc., Sparks, NV (US)

( * ) Notice: Subject to any disclaimer, the term of this patent is extended or adjusted under 35 U.S.C. 154(b) by 327 days.

(21) Appl. No.: 15/959,807

(22) Filed: Apr. 23, 2018

(65) Prior Publication Data

US 2018/0313800 A1 Nov. 1, 2018

Related U.S. Application Data

(60) Provisional application No. 62/490,227, filed on Apr. 26, 2017.

(51) Int. Cl.
*G01N 33/00* (2006.01)
*G01N 25/00* (2006.01)
(Continued)

(52) U.S. Cl.
CPC ......... *G01N 33/0016* (2013.01); *G01N 25/18* (2013.01); *G01N 25/22* (2013.01);
(Continued)

(58) Field of Classification Search
CPC ........... G01N 33/0016; G01N 33/0013; G01N 27/125; G01N 27/123; G01N 25/18; G01N 25/22; G01N 25/48
See application file for complete search history.

(56) References Cited

U.S. PATENT DOCUMENTS

| 5,019,885 A | 5/1991 | Yagawara et al. |
| 5,464,966 A | 11/1995 | Gaitan et al. |
(Continued)

FOREIGN PATENT DOCUMENTS

| EP | 2278308 A1 | 1/2011 |
| EP | 2878944 A1 | 6/2015 |
(Continued)

OTHER PUBLICATIONS

Dong, Ki-Young et al. "Detection of a CO and NH3 gas mixture using carboxylic acid-functionalized single-walled nanotubes." Nanoscale Research Letters (2013) 8 12. (Year: 2013).*
(Continued)

*Primary Examiner* — Christopher Adam Hixson
(74) *Attorney, Agent, or Firm* — TraskBritt

(57) ABSTRACT

A microhotplate comprising a membrane suspended over a substrate by a plurality of tethers connected between the substrate and the membrane. The membrane comprises a resistive heater comprising an electrically conductive material having a varying width from a peripheral portion of the membrane to a center of the membrane. The electrically conductive material comprises a first portion spiraling in a first direction and a second portion spiraling in a second direction and in electrical communication with the first portion at the center of the membrane. The microhotplate further comprises a first electrically conductive trace extending over a first tether and in electrical contact with a bond pad on the substrate and the first portion and a second electrically conductive trace extending over another tether and in electrical contact with another bond pad on the substrate and the second portion. Related chemical sensors and related methods of detecting at least one analyte are also disclosed.

24 Claims, 12 Drawing Sheets

(51) Int. Cl.
　　*G01N 27/00*　　　(2006.01)
　　*B01L 3/00*　　　　(2006.01)
　　*G01N 25/18*　　　(2006.01)
　　*G01N 25/22*　　　(2006.01)
　　*G01N 25/48*　　　(2006.01)
　　*G01N 27/12*　　　(2006.01)
(52) U.S. Cl.
　　CPC ........... *G01N 25/48* (2013.01); *G01N 27/125* (2013.01); *G01N 33/0013* (2013.01); *B01L 2300/0645* (2013.01); *B01L 2300/12* (2013.01); *B01L 2300/16* (2013.01); *B01L 2300/1827* (2013.01); *G01N 27/123* (2013.01)

(56) References Cited

U.S. PATENT DOCUMENTS

| | | |
|---|---|---|
| 7,849,727 B2 | 12/2010 | Gardner et al. |
| 7,928,343 B2 | 4/2011 | King et al. |
| 8,719,960 B2 | 5/2014 | King |
| 8,931,950 B2 | 1/2015 | King et al. |
| 9,182,366 B2 | 11/2015 | Izawa et al. |
| 9,228,967 B2 | 1/2016 | Alepee et al. |
| 2004/0075140 A1 | 4/2004 | Baltes et al. |
| 2006/0194332 A1 | 8/2006 | Wado et al. |
| 2009/0151429 A1 | 6/2009 | Jun et al. |
| 2009/0312954 A1 | 12/2009 | Utrianinen |
| 2011/0268148 A1 | 11/2011 | King et al. |
| 2012/0297860 A1 | 11/2012 | Izawa et al. |
| 2015/0212030 A1 | 7/2015 | Alepee et al. |

FOREIGN PATENT DOCUMENTS

| | | |
|---|---|---|
| EP | 2975386 A1 | 1/2016 |
| GB | 2533294 A | 6/2016 |
| JP | 2008-304293 A | 12/2008 |
| WO | 20150132563 A1 | 9/2015 |

OTHER PUBLICATIONS

Aigner et al., Si-planar-pellistor: designs for temperature modulated operation, Sensors and Actuators B 33, Jun. 25, 1996, pp. 151-155, vol. 33, Issues ♪ 3, Elsevier B.V.

Ali et al., Tungsten-Based SOI Microhotplates for Smart Gas Sensors, Journal of Microelectromechanical Systems, Dec. 2008, pp. 1408-1417, vol. 17, No. 6.

International Written Opinion from International Application No. PCT/US2018/028935, dated Aug. 21, 2018, 13 pages.

International Search Report from International Application No. PCT/US2018/028935, dated Aug. 21, 2018, 3 pages.

European Partial Search Report from European Application No. 18790558.3, dated Jan. 18, 2021, 17 pages.

European Supplementary Search Report from European Application No. 18790558.3, dated Apr. 6, 2021, 13 pages.

Velmathi G. et al., "Design, Electro-Thermal simulation and geometrical optimization of double spiral shaped microheater on a suspended membrane for gas sensing", IECON 2010—36th Annual Conference on IEEE Industrial Electronics Society, IEEE, Piscataway, NJ, USA (Nov. 2010), pp. 1258-1262.

\* cited by examiner

GAS SENSORS INCLUDING MICROHOTPLATES WITH RESISTIVE HEATERS, AND RELATED METHODS

PRIORITY CLAIM

This application claims the benefit of the filing date of U.S. Provisional Patent Application Ser. No. 62/490,227, filed Apr. 26, 2017, for "MICROHOTPLATES WITH RESISTIVE HEATERS, GAS SENSORS INCLUDING THE MICROHOTPLATES, AND RELATED METHODS."

TECHNICAL FIELD

Embodiments of the disclosure relate generally to micro-electro-mechanical systems (MEMS), such as microhotplate devices, gas sensors including the microhotplate devices, and to related methods of forming and operating the microhotplate devices and gas sensors. More particularly, embodiments of the disclosure relate to microhotplates having resistive heaters configured to uniformly heat a membrane of the microhotplate while reducing power consumption and localized overheating in the structure of the microhotplate, to related methods of operating the microhotplates, and to related methods of fabricating the microhotplates.

BACKGROUND

Microhotplates may be useful in sensors used for chemical detection applications. Microhotplates may include a chemical sensitive coating for detecting one or more properties of one or more gases or analytes. The microhotplates may be sized to have dimensions on the order of tens to hundreds of microns to consume less power and be more easily integrated into smaller packages than existing microhotplate devices measuring many hundreds of microns. Microhotplates may be formed using MEMS-based or CMOS-based silicon processes.

Conventional heating elements associated with a microhotplate may provide a heat source for heating a suspended membrane of the microhotplate or a material disposed over the heating element (e.g., the chemical sensitive coating). However, due to differences in thermal losses to portions of the microhotplate away from the membrane, the heating element and any chemical sensitive coating materials associated with the heating element often exhibit different temperatures, resulting in a non-uniform temperature profile across the microhotplate. By way of non-limiting example, peripheral portions of the membrane supporting the heating element may lose relatively more heat than central portions thereof, resulting in a non-uniform temperature profile across the heating element and the membrane. For example, in some instances, the peripheral portions often exhibit greater convection than central portions of the membrane, resulting in more heat loss from the peripheral portions to than from the central portions of the membrane. In addition, heat losses from the suspended microhotplate to its supporting substrate by conduction through supporting tethers may further exacerbate the non-uniformity of the temperature profile of the microhotplate. Furthermore, chemical reactions on the chemical sensitive coating material, as well as physical measurements made on uncoated plate surfaces of a reference microhotplate (such as, for example, for thermal conductivity measurements) may be sensitive to temperature changes, and performance of an associated sensor may be negatively impacted by a non-uniform operating temperature of the microhotplate.

In order to compensate for non-uniform heat losses across the microhotplate, some microhotplates incorporate a heat spreader plate to facilitate somewhat uniform heat transfer through the membrane. Other devices include heating elements having unique shapes including sharp corners and abrupt changes in direction. However, such sharp corners and abrupt changes in direction may adversely affect the operation and lifetime of the resistive heater.

BRIEF SUMMARY

Embodiments disclosed herein include microhotplates, chemical sensors including at least one microhotplate, and methods of detecting at least one analyte. For example, in accordance with one embodiment, a microhotplate comprises a membrane suspended over a substrate by a plurality of tethers connected between the substrate and the membrane. The membrane comprises a resistive heater comprising an electrically conductive material having a varying width from a peripheral portion of the membrane to a center of the membrane. The electrically conductive material comprises a first portion spiraling in a first direction, and a second portion spiraling in a second direction and in electrical contact with the first portion at the center of the membrane. The microhotplate further comprises a first electrically conductive trace extending over a first tether and in electrical contact with a bond pad on the substrate and the first portion and a second electrically conductive trace extending over another tether and in electrical contact with another bond pad on the substrate and the second portion.

In additional embodiments, a chemical sensor comprises at least one microhotplate. The at least one microhotplate comprises a plurality of tethers extending over a void formed in a substrate, the plurality of tethers supporting the membrane over the substrate and comprising a plurality of dielectric layers. The membrane comprises a resistive heater between two dielectric layers of the plurality of dielectric layers, the resistive heater comprising an electrically conductive material having a first portion spiraling in a first direction and a second portion spiraling in a second, opposite direction, the electrically conductive material having a varying width from an outer portion of the resistive heater to a central portion thereof. The microhotplate further comprises electrically conductive heater traces configured to provide power to the resistive heater, the electrically conductive heater traces overlying at least one of the tethers.

In further embodiments, a method of measuring at least one of a thermal conductivity, an exothermic event, and an endothermic event comprises providing a current to a resistive heater of at least one microhotplate, the resistive heater comprising a varying width from a peripheral portion thereof toward a center thereof, the resistive heater comprising a first portion extending from the peripheral portion toward the center thereof and spiraling in a clockwise direction and a second portion in contact with the first portion at the center of the resistive heater and extending from the center of the resistive heater toward the peripheral portion thereof and spiraling in a counterclockwise direction. The method further comprises measuring a voltage and current across the resistive heater and calculating a resistance of the resistive heater to determine an average temperature of the resistive heater.

In yet other embodiments, a sensor for providing orthogonal analysis of a sample comprises an array of microhotplates. Each microhotplate comprises a resistive heater comprising an electrically conductive material having a varying width from a peripheral portion of the membrane to a center of the membrane. The electrically conductive material comprises a first portion spiraling in a first direction, and a second portion spiraling in a second direction and in electrical contact with the first portion proximate the center of the membrane. The sensor further comprises a controller configured to determine one or more of at least one property of the resistive heater of at least one microhotplate of the array of microhotplates and a resistance between interdigitated electrodes of at least one microhotplate of the array of microhotplates.

In yet further embodiments, a method of measuring a response from a sensor comprising an array of microhotplates comprises providing a current to a resistive heater of each microhotplate of an array of microhotplates, the resistive heater of each microhotplate having a varying width from a peripheral portion of the membrane to a center of the membrane. The electrically conductive material comprises a first portion spiraling in a first direction, and a second portion spiraling in a second direction and in electrical contact with the first portion proximate the center of the membrane. The method further comprises measuring a response from each microhotplate of the array of microhotplates, wherein measuring a response from each microhotplate of the array of microhotplates comprises analyzing a response from at least one reference microhotplate free of a coating material or comprising an inert material overlying a dielectric material over its resistive heater, analyzing a response from at least one microhotplate comprising a catalytic material overlying a dielectric material over its resistive heater, and analyzing a response from at least one microhotplate comprising a chemical sensing material selected from the group consisting of a p-type semiconductor, an n-type semiconductor, and an ionic conductor overlying a dielectric material over its resistive heater.

DETAILED DESCRIPTION

Figure 1A:
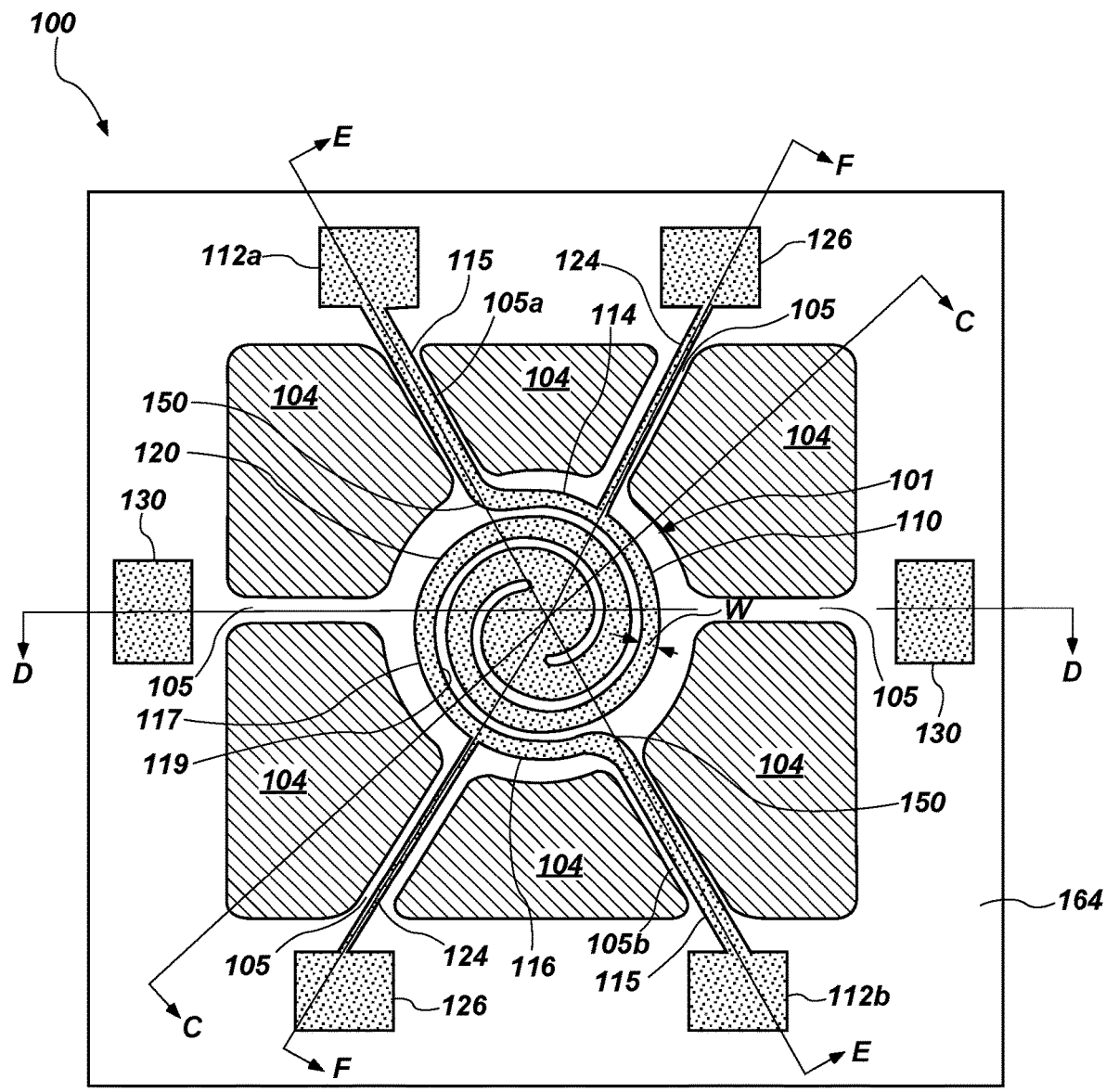
FIG. 1A is a top cross-sectional view of a microhotplate taken along section line A-A shown in FIG. 1C, in accordance with embodiments of the disclosure.

Illustrations presented herein are not meant to be actual views of any particular material, component, or system, but are merely idealized representations that are employed to describe embodiments of the disclosure.

The following description provides specific details, such as material types, material thicknesses, and processing techniques in order to provide a thorough description of embodiments described herein. However, a person of ordinary skill in the art will understand that the embodiments disclosed herein may be practiced without employing these specific details. Indeed, the embodiments may be practiced in conjunction with conventional fabrication techniques employed in the industry.

As used herein, the term "tether" means and includes a structure that supports a portion of a membrane of a device over a substrate. A tether may extend from a peripheral portion of a device to a membrane of a microhotplate and may suspend the membrane over the substrate of the device. The tether may be suspended over a void formed in the substrate.

As used herein, the term "membrane" means and includes a central portion of a microhotplate, which may be suspended over a substrate by one or more tethers. The one or more tethers may extend from a peripheral portion of a sensor to the membrane, wherein the membrane is suspended over a cavity in a substrate by the tethers.

According to embodiments described herein, a microhotplate includes a membrane suspended over a substrate by a plurality of tethers extending from the membrane to a portion of the substrate. The membrane may be separated from the substrate by a void (e.g., a cavity) formed in a portion of the substrate. The membrane may be supported over the void in the substrate by the plurality of tethers extending from a periphery of the void in the substrate to the membrane. The depth of the cavity may be precisely controlled to modify the sensitivity and power consumption of the sensor. A more shallow depth may increase the conductive heat losses to the substrate, which may increase the sensitivity of the sensor to surrounding gas thermal conductivity. An increased depth may reduce losses to the substrate and may be desirable for increased efficiency and decreased sensitivity to the surrounding environment. In other words, the depth of the substrate relative to the tethers may be decreased to increase conduction heat losses to the substrate, which may improve determination of at least one property (e.g., a thermal conductivity) of a gas proximate the microhotplate.

The membrane may comprise a resistive heater shaped and configured to provide a substantially uniform temperature profile (e.g., an isothermal temperature profile) across the microhotplate. In some embodiments, the tethers and the membrane may be formed of and include the same materials. The resistive heater may comprise an electrically conductive material having a spiral shape and extending from a pair of bond pads located on the substrate and configured to provide a current through the resistive heater. The electrically conductive material may comprise a varying (e.g., an increasing, a continuously increasing) width along a length thereof as the electrically conductive material spirals from an outer portion (e.g., a periphery) of the membrane toward an inner portion (e.g., the center) of the membrane. As used herein, the term "varying" when used to describe a width of a structure means that the width changes along a length of the structure. The width may change in stepped increments, may change substantially continuously, may be tapered, may change substantially continuously over some portions and may change in stepped portions in other portions, etc. The varying width of the electrically conductive material may change a localized resistance (and hence a local heat output) of the electrically conductive material, thereby providing a substantially uniform temperature profile across the membrane and associated materials (e.g., a chemical sensing material, a catalyst coating, an inert coating, etc., of the membrane) disposed on the microhotplate. The electrically conductive material may comprise a first portion extending from an intersection between a first tether and the membrane and spiraling from an outer portion of the membrane toward the center of the membrane, the first portion spiraling in a first direction (e.g., a clockwise direction). The electrically conductive material may further comprise a second portion extending from an intersection between a second tether and the membrane and spiraling from an outer portion of the membrane toward the center of the membrane. The second portion may spiral in a second direction opposite the first direction (e.g., the second portion may spiral in a counter-clockwise direction). The first portion and the second portion may be in electrical communication at the central portion of the membrane. The electrically conductive material may reverse direction of rotation at the center of the membrane, at a location where the first portion contacts the second portion.

Portions of the resistive heater having a relatively smaller width may exhibit a relatively greater electrical resistance than portions of the resistive heater with a relatively greater width. The portions of the resistive heater exhibiting the greater electrical resistance may generate more heat than portions having a relatively smaller electrical resistance. Portions of the resistive heater with a relatively smaller width may be located at locations of the resistive heater that are subject to relatively greater heat loss, such as at peripheral portions of the membrane, whereas portions of the resistive heater with a relatively greater width may be located at locations of the resistive heater that are not subject to as great a heat loss (e.g., at central portions of the membrane). The resistive heater may be sized and shaped such that the membrane exhibits a substantially uniform temperature profile, even though peripheral portions of the membrane may be subject to greater heat losses than central portions thereof.

The resistive heater may be free of sharp corners and abrupt changes in direction, that can lead to current crowding and high current densities, which in turn, may cause an undesired phenomenon known as "electromigration" wherein atoms of the resistive heater redistribute, leading to an effective thinning of the resistive heater in certain regions as atoms migrate to other regions of the resistive heater and ultimately leading to a non-uniform temperature profile and failure of the resistive heater. Forming the resistive heater with the varying (e.g., continuously varying) width may substantially reduce negative effects, such as electromigration, exacerbated by regions of high current density, high temperature, or both. In addition, the resistive heaters described herein may reduce the power required to heat the associated microhotplates to a desired temperature. In some embodiments, such as where the resistive heaters are used in microhotplate devices configured to measure a thermal conductivity, the heat transfer from the microhotplate to the environment proximate the microhotplate may be increased relative to conventional microhotplates. In addition, heat losses from the tethers to the extending substrate may be reduced compared to conventional microhotplates. The microhotplates including the resistive heaters with a varying width may be operated at temperatures between about 200° C. and about 1,200° C., such as between about 300° C. and about 800° C., or between about 800° C. and about 1,200° C. In some embodiments, the microhotplates are operated at temperatures up to about 1,200° C. without damaging the microhotplate (e.g., causing failure of the resistive heater or the membrane). By way of comparison, prior art microhotplates may fail at temperatures of greater than about 500° C., at least partially due to areas that become depleted in atoms due to electromigration.

A sensor may include a plurality of microhotplates. As described herein, at least some of the microhotplates may be configured to measure a thermal conductivity of a sample (e.g., a gaseous analyte, a concentration of an analyte in a sample, etc.), at least some of the microhotplates may be configured to determine a temperature at which the sample exhibits one or more reactions, and at least some of the microhotplates may be configured to include one or more coatings configured to interact with particular components that may be contained in the sample (e.g., may include one or more metal oxide semiconductor coatings formulated and configured to interact with particular species that may be contained within the sample). The use of a plurality of microhotplates in the sensor may increase a range of analytes that may be detected using the sensor and may increase the sensitivity and selectivity of the sensor. By way of non-limiting example, the plurality of microhotplates may be used to perform orthogonal analysis of the sample and determine one or more of a composition of the sample, a concentration of one or more gases in the sample, or another property of the sample.

Figure 1B:
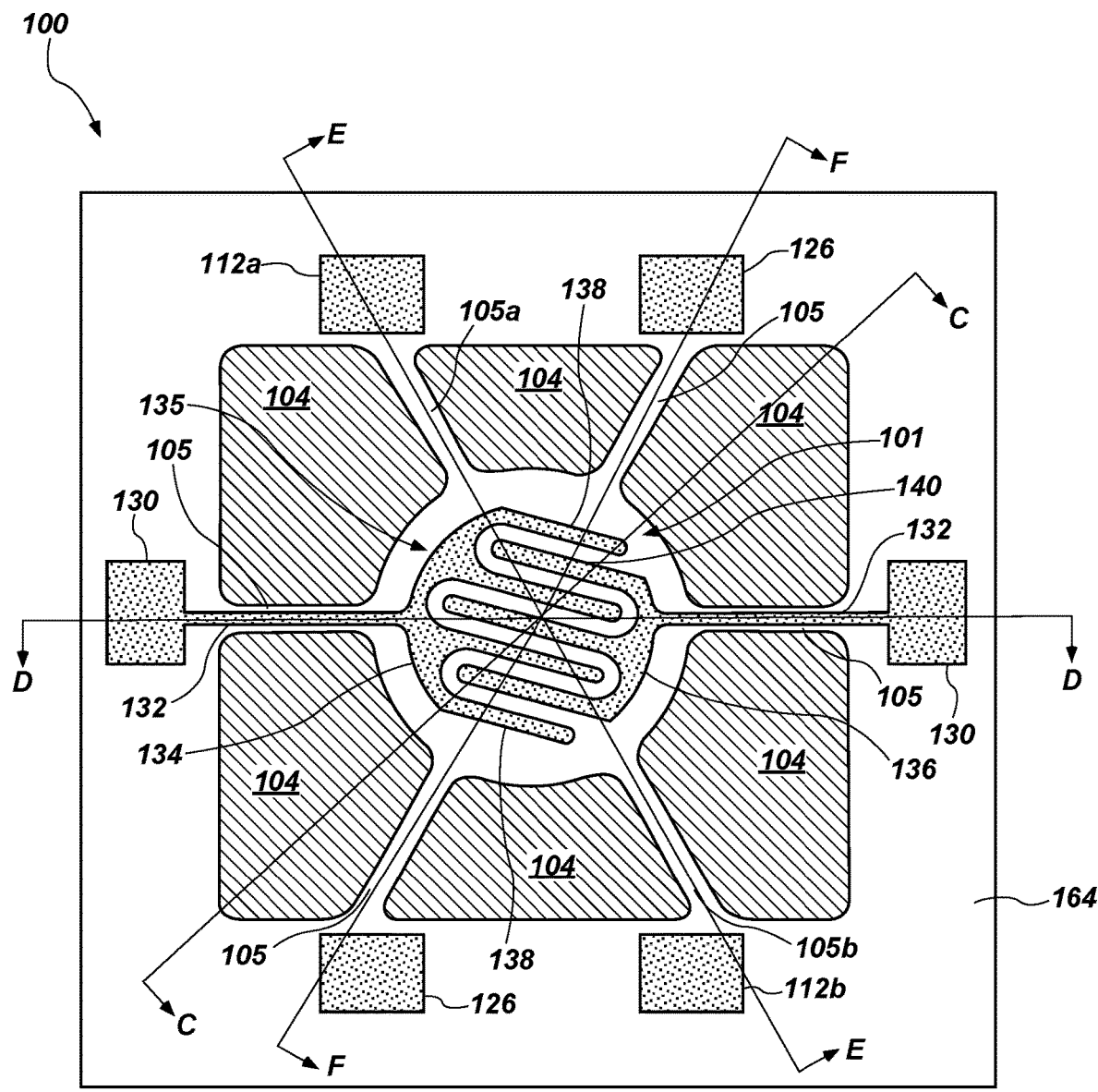
FIG. 1B is a top cross-sectional view of the microhotplate taken along section line B-B shown in FIG. 1D, in accordance with embodiments of the disclosure.
Figure 1C:
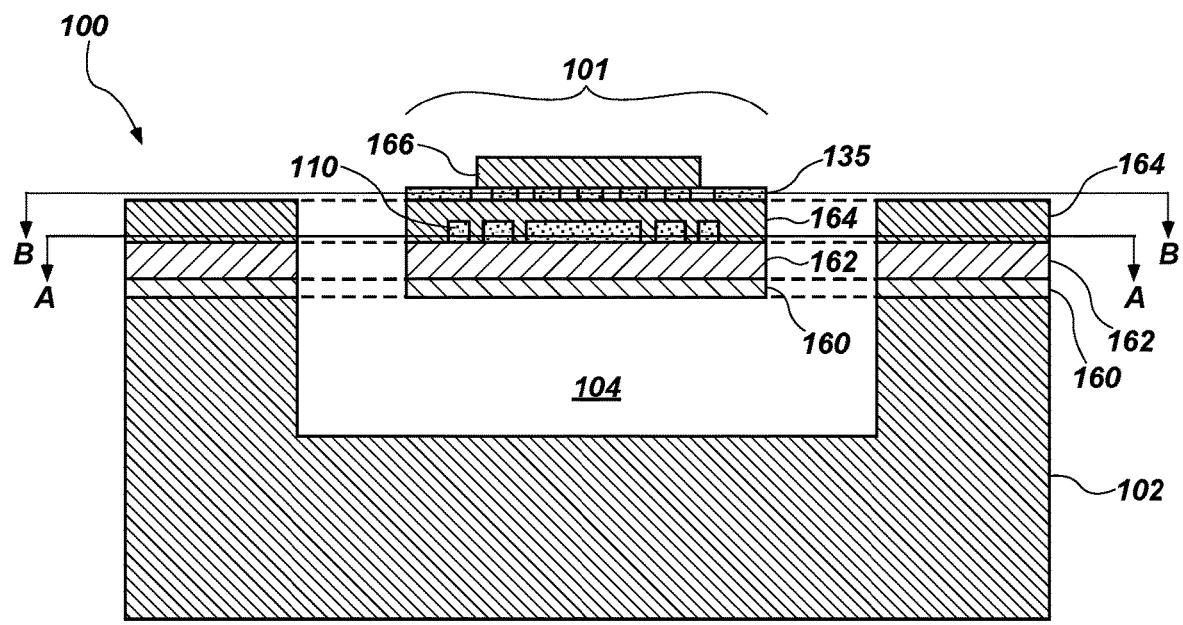
FIG. 1C is a side cross-sectional view of the microhotplate of FIG. 1A taken along section line C-C in FIG. 1A.

FIG. 1A is a top view of a device 100 comprising a microhotplate according to one embodiment of the disclosure. The device 100 comprises a membrane 101 formed over a substrate 102 (FIG. 1C). The substrate 102 may be a conventional silicon substrate or other bulk substrate including semiconductor material. As used herein, the term "substrate" means and includes not only silicon wafers, but also silicon-on-insulator ("SOI") substrates, such as silicon-on-sapphire ("SOS") substrates or silicon-on-glass ("SOG") substrates, epitaxial layers of silicon on a base semiconductor foundation, or other semiconductor materials. In some embodiments, the substrate 102 comprises silicon. In other embodiments, the substrate 102, or at least a portion thereof, may be oxidized and comprise, for example, a silicon oxide (e.g., $SiO_2$).

The membrane 101 may have a circular shape, a square shape, a rectangular shape, a polygonal shape (e.g., a pentagonal shape, a hexagonal shape, an octagonal shape, etc.), or another shape. The membrane 101 may be supported over the substrate 102 by a plurality of tethers 105, 105a, 105b. In some embodiments, the device 100 may comprise six tethers 105, although the disclosure is not so limited. In other embodiments, the device 100 includes any number of tethers 105, such as three tethers 105, four tethers 105, five tethers 105, six tethers 105, seven tethers 105, eight tethers 105, or any other number of tethers 105. In some embodiments, the device 100 comprises an odd number of tethers 105. Where the membrane 101 comprises a polygonal shape, corners (e.g., points) of the polygonal shape may be centered over a respective tether 105. For example, and with reference to FIG. 2, a device 200 may comprise a hexagonally-shaped membrane 201. Points of the membrane 201 may be disposed over a portion of a respective tether 105. In some embodiments, the points of the polygonal shape are disposed over a central portion of the respective tether 105.

The tethers 105 may extend from a peripheral portion of the device 100 (e.g., from the substrate 102) to the membrane 101 over a void 104 formed in the substrate 102. In other words, the tethers 105 may extend from the substrate 102 to the membrane 101. The tethers 105 may support the membrane 101 over the substrate 102. The membrane 101 may be separated from the substrate by the void 104, as shown in, for example, FIG. 1C. The tethers 105 may be separated from a portion of (e.g., a central portion of) the substrate 102 by the void 104.

The tethers 105 may have a width selected to reduce (e.g., minimize) a net heat flux along a length thereof and to reduce heat losses to the substrate 102. By way of non-limiting example, a width of the tethers 105 may be minimized to reduce heat loss from the periphery of the membrane 101 via conduction. However, the width of the tethers 105 may be large enough to provide sufficient mechanical support to the membrane 101, such as during heating thereof. Accordingly, the tethers 105, 105a, 105b may reduce heat losses from the membrane 101 through the tethers 105, 105a, 105b to the underlying substrate 102 compared to conventional microhotplate devices. In some embodiments, the tethers 105 may include a widened portion proximate the intersection of the tethers 105 and the membrane 101, the widened portion having a relatively greater width than other portions of the tether 105. In some embodiments, the tethers 105 may also include a widened (e.g., a filleted) portion proximate an intersection of the tethers 105 and substrate 102. Such filleting may reduce a corner stress concentration of the tethers 105. In some embodiments, a width of the tethers 105 may be between about 3 µm and about 20 µm, such as between about 3 µm and about 15 µm, or between about 5 µm and about 10 µm. As used herein, the term "fillet" means and includes a rounding of an interior or exterior corner, such as where the tethers 105 intersect the membrane 101. By way of non-limiting example, a filleted shape, as used herein, may have a shape similar to a shape of a fillet weld or a double tangent arc.

With continued reference to FIG. 1A, the device 100 may include a resistive heater 110 comprising an electrically conductive trace 115 electrically coupled to a pair of bond pads 112a, 112b. The resistive heater 110 may be powered by application of a current between the bond pads 112a, 112b. The resistive heater 110 may have a substantially circular shape. In other embodiments, the resistive heater 110 may exhibit an oval shape, a circular shape, or an elliptical shape. A resistive heater 110 with a circular shape may provide a substantially uniform temperature profile across the resistive heater 110.

The electrically conductive trace 115 may extend from a first bond pad 112a over a surface of a first tether 105a to the resistive heater 110 at the membrane 101. Another electrically conductive trace 115 may extend from a second bond pad 112b over a surface of a second tether 105b to the resistive heater 110 at the membrane 101. In some embodiments, the first tether 105a and the second tether 105b may be located substantially opposite one another and the first bond pad 112a and the second bond pad 112b may be located substantially opposite one another. The electrically conductive traces 115 may also be referred to herein as "electrically conductive heater traces."

Portions of the electrically conductive trace 115 over the tethers 105 may be substantially linear. At an intersection of the first tether 105a and the membrane 101, the electrically conductive trace 115 may transition from a linear shape to a curved (e.g., spiral, winding, rotating, etc.) shape. Similarly, at an intersection of the second tether 105b and the membrane 101, the electrically conductive trace 115 may transition from a linear shape to a curved (e.g., spiral, winding, rotating, etc.) shape.

The resistive heater 110 may comprise a first portion 114 extending from an outer portion (e.g., a periphery) of the membrane 101 proximate the first tether 105a to a location proximate the center of the membrane 101 and a second portion 116 extending from the periphery of the membrane 101 proximate the second tether 105b to a location proximate the center of the membrane 101. The first portion 114 and the second portion 116 may be in electrical contact with each other at a central portion of the membrane 101.

In some embodiments, a first surface (e.g., a radially varying outer surface) 117 and a second surface (e.g., a radially varying inward surface) 119 opposing the first surface 117 of portions of the resistive heater 110 may not be substantially parallel. Stated another way, opposing portions of the first surface 117 and the second surface 119 may not be parallel. In some embodiments, the first portion 114 and the second portion 116 each comprise a spiral shape and the first surface 117 and the second surface 119 comprise curved (e.g., arcuate) surfaces. Accordingly, outer surfaces of the resistive heater 110 may comprise arcuate surfaces.

The first portion 114 may comprise a spiral shape and may spiral (e.g., wind, rotate, coil, curl, twist, etc.) in a first direction (e.g., one of a clockwise direction or a counter-clockwise direction). The second portion 116 may comprise a spiral shape and may spiral (e.g., wind, rotate, coil, curl, twist, etc.) in a second direction opposite the first direction (e.g., another of the clockwise direction and the counter-clockwise direction). In some embodiments, the direction of the spiral may change proximate the center of the membrane 101 where the first portion 114 and the second portion 116 contact each other. Stated another way, at the center of the membrane 101, a direction of rotation of the resistive heater 110 may change from a first direction to a second, opposite direction.

Radially adjacent regions of the first portion 114 may be isolated from each other by a same distance. Similarly, radially adjacent regions of the second portion 116 may be isolated from each other by a same distance. In some embodiments, a region of the second portion 116 may be disposed between radially adjacent regions of the first portion 114 and a region of the first portion 114 may spiral and be disposed between radially adjacent portions of the second portion 116. In other words, coils (e.g., spirals) of the first portion 114 may be radially surrounded by coils (e.g., spirals) of the second portion 116 and coils of the second portion 116 may be radially surrounded by coils of the first portion 114. Stated another way, coils of the first portion 114 and coils of the second portion 116 may intertwine with each other and may be separated from each other by a distance.

In some embodiments, a gap 120 between adjacent portions of the first portion 114 and the second portion 116 may be substantially constant. The gap 120 may exhibit a spiral shape, similar to the spiral shape of the first portion 114 and the second portion 116. The gap 120 may have a substantially constant width. In some embodiments, the width of the gap 120 may be less than a width W of the resistive heater 110 (e.g., less than the narrowest width W). In some embodiments, the width of the gap 120 may be minimized to facilitate a uniform temperature profile across the microhotplate or the membrane 101, such as by using the resistive heater 110 as a heat spreader. By way of non-limiting example, a width of the gap 120 may be minimized such that a distance between adjacent portions of the resistive heater 110 is reduced. Since the resistive heater 110 exhibits a greater thermal conductivity than, for example, a dielectric material disposed over the resistive heater 110 and in the gaps 120, the resistive heater 110 may approximate a heat spreader when the gaps 120 comprise a substantially reduced width. In some embodiments, the gap 120 may have a width between about 0.5 µm and about 5.0 µm, such as between about 1.0 µm and about 4.0 µm, between about 1.5 µm and about 3.5 µm, or between about 2.0 µm and about 3.0 µm. In some embodiments, the width of the gap 120 may be about 3.0 µm. In other embodiments, the width of the gap 120 may vary from portions proximate the periphery of the membrane 101 to portions proximate the center of the membrane 101. In some embodiments, a width of the gap 120 may be greater at radially inward portions that at radially outward portions of the resistive heater 110.

The electrically conductive material of the resistive heater 110 may comprise a metallization layer such as, for example, tungsten, molybdenum, tantalum, platinum, palladium, aluminum, titanium, titanium tungsten (TiW), copper, gold, doped silicon, doped polysilicon, other conductive metals or alloys, combinations thereof, or a layered structure comprising one or more of the aforementioned materials. The layered structure may include, for example, a first layer comprising one or more of tungsten, molybdenum, tantalum, platinum, palladium, aluminum, titanium, titanium tungsten (TiW), copper, gold, doped silicon, doped polysilicon, other conductive metals or alloys and at least a second layer comprising another of tungsten, molybdenum, tantalum, platinum, palladium, aluminum, titanium, titanium tungsten (TiW), copper, gold, doped silicon, doped polysilicon, other conductive metals or alloys over the first layer. In some embodiments, the resistive heater 110 may include one or more adhesion layers (e.g., titanium, tungsten, a combination thereof, etc.) configured to improve adhesion to one or more insulating materials underlying or overlying the resistive heater 110, to vary the composite resistive properties of the resistive heater 110, or both. In some embodiments, and at least another metallization layer and/or at least one passivation layer may overlie the one or more adhesion layers. In some embodiments, the electrically conductive material comprises tungsten. In some such embodiments, the resistive heater 110 may be operated at temperatures up to 1,200° C. without damaging the device 100.

The first portion 114 may exhibit a varying (e.g., an increasing, a continuously increasing, a tapered) width W from a location proximate a periphery of the membrane 101 to a location proximate the center of the membrane 101. The first portion 114 may exhibit an increasing width W from outer portions of the membrane 101 toward the center of the membrane 101. In some embodiments, the width W increases from a minimum width proximate the periphery of the membrane 101 (e.g., proximate a widened portion 150 of the first portion 114) to a maximum width proximate the center of the membrane 101. The width W may increase substantially continuously from the outer portion of the membrane 101 to the inner portion thereof. Similarly, the second portion 116 may exhibit a varying (e.g., an increasing, a continuously increasing, a tapered) width from the outer portion of the membrane 101 (e.g., proximate an intersection between the second tether 105b and the membrane 101) toward the center of the membrane 101.

In some embodiments, the width of each location of the resistive heater 110 may be related to a distance of each location of the resistive heater 110 from a center of the membrane 101. By way of non-limiting example, where the membrane 101 comprises a circular shape, the resistive heater 110 may have a decreasing width as a radial distance from the center of the membrane 101 increases. Since the resistive heater 110 comprises a spiral shape with a changing (e.g., continuously changing) distance from the center of the membrane 101, the width of the resistive heater 110 may change (e.g., continuously change) along a length thereof.

In some embodiments, a maximum width of the resistive heater 110 (e.g., a width at the center thereof) may be at least about 2.5 times a minimum width of the resistive heater 110 (e.g., a width proximate the widened portion 150). In some embodiments, the maximum width is greater than about 3.0 times the minimum width, greater than about 3.5 times the minimum width, greater than about 4.0 times the minimum width, or even greater than about 5.0 times the minimum width of the resistive heater 110.

In some embodiments, for a predetermined first distance from the center of the membrane 101, the width of the resistive heater 110 may be greater at substantially all distances (e.g., radial distances) from the center that are less than the first distance and may be smaller at substantially all distances from the center that are more than the first radial distance. By way of non-limiting example, the width of the resistive heater 110 as a function of distance from the center of the membrane may be approximated by, for example, Equation (1) below:

$$W_r = r \times A \quad (1)$$

wherein $W_r$ is the width of the resistive heater 110 for a predetermined distance from the center of the membrane 101, r is the distance from the center of the membrane 101, and A is a constant.

In other embodiments, the width of the resistive heater 110 may increase as the resistive heater 110 approaches the center of the membrane 101 according to a continuously differentiable formula. In some such embodiments, the resistive heater 110 may exhibit a shape such that its derivative exists at each point along the resistive heater 110, thereby reducing and, in some embodiments, eliminating any sharp corners in the resistive heater 110. In some such embodiments, the resistive heater 110 may not include any sharp corners (e.g., such as a 90° corner, a vertex, an angular point of a polygon, etc.) or abrupt changes in direction. Stated another way, the resistive heater 110 may not include abrupt changes in direction or sharp corners, such as a square corner. In other words, the resistive heater 110 may not comprise a corner converging at a single point (e.g., such as at a vertex). Rather, the resistive heater 110 may comprise arcuate (e.g., curved) surfaces, such as the first surface 117 and the second surface 119. Accordingly, the resistive heater 110 may be substantially free of corners. Stated another way, the side surfaces (e.g., the first surface 117 and the second surface 119) may be substantially free of corners and may comprise arcuate surfaces.

In some embodiments, the resistive heater 110 exhibits an Archimedean Spiral shape that may be offset to create the gap 120 between the first portion 114 and the second portion 116.

The width W of the resistive heater 110 may increase from about 3 μm at a location proximate the periphery of the membrane 101 to about 20 μm at a location proximate the center of the membrane 101.

In some embodiments, the resistive heater 110 may include a widened portion 150 at a location where the electrically conductive trace 115 transitions into the resistive heater 110 at a peripheral portion of the membrane 101 (which region may be referred to herein as a "transition region"). In some embodiments, the widened portion 150 may facilitate a transition from the substantially linear shape of the electrically conductive trace 115 on the tether 105 to the spiral shape of the resistive heater 110. In some such embodiments, the resistive heater 110 may have a localized wide area at the widened portion 150, a relatively smaller width radially inward from the widened portion 150 and an increasing (e.g., continuously increasing) width as the resistive heater 110 spirals toward the center of the membrane 101.

The widened portion 150 may substantially reduce the current density at the transition region and reduces electromigration, enhancing the lifetime and overall operation of the resistive heater 110. In other words, the widened portion 150 may facilitate an improved current density and a reduction in electromigration proximate the region where the electrically conductive material of the resistive heater 110 transitions from the linear portion over the tethers 105a, 105b (e.g., the electrically conductive traces 115) to the resistive heater 110.

The resistive heater 110 may be formed by a lithographic process. By way of non-limiting example, a reticle having a pattern of the resistive heater 110 may be used to form (e.g., deposit and pattern) the material of the resistive heater 110.

In some embodiments, an electrical resistance of the resistive heater 110 may be related to the width W thereof. The electrical resistance of the resistive heater 110 may be relatively greater in magnitude at portions of the resistive heater 110 that have a smaller width W than at portions of the resistive heater 110 having a relatively larger width W (e.g., at portion proximate the center of the membrane 101 (i.e., radially inward portions)).

Increasing the width of the resistive heater 110 from the outer portions of the membrane 101 to the central portion of the membrane 101 may facilitate a substantially uniform temperature profile across the resistive heater 110 and the associated membrane 101. At the peripheral portions, the membrane 101 and the resistive heater 110 may exhibit a greater heat loss than at central portions thereof. Accordingly, the electrical resistance of the resistive heater 110 may be greater at locations having a relatively smaller width (e.g., at locations proximate the periphery of the membrane 101) than at locations having a relatively greater width (e.g., at locations proximate the center of the membrane 101). Thus, the resistive heater 110 (and the membrane 101) may exhibit a substantially uniform temperature profile since outer portions of the membrane 101 that are subject to greater heat losses are heated more by the resistive heater 110 than the central portions thereof. In other words, the tapered width of the resistive heater 110 may create a substantially isothermal temperature profile across the resistive heater 110 and the membrane 101. In addition, since the resistive heater 110 provides a substantially uniform temperature profile of the membrane 101, compared to conventional microhotplates, the device 100 may use less power to heat the membrane 101. Further, the reduced width of the tethers 105, 105a, 105b may reduce conductive heat losses from the membrane 101 to the substrate 102.

With continued reference to FIG. 1A, the device 100 may further include sense lines 124 configured to measure a voltage drop across the resistive heater 110. The sense lines 124 may be located at a location such that the average temperature of an active area of the resistive heater 110 may be determined by measuring the voltage drop across the resistive heater 110 with the sense lines 124. The sense lines 124 may comprise a high impedance voltage measurement system such that there is substantially no voltage drop through the sense lines 124. The sense lines 124 may also be referred to herein as "electrically conductive sense line traces."

The sense lines 124 may be coupled to respective sense line bond pads 126. The sense line bond pads 126 may be located on the substrate 102 at a periphery of the device 100. The sense lines 124 may extend from the sense line bond pads 126 to the resistive heater 110. The sense lines 124 may extend over opposing tethers 105, which may be different tethers 105 than the tethers 105a, 105b over which the electrically conductive traces 115 extend.

The device 100 may further include another pair of bond pads 130. With reference to FIG. 1B, each bond pad 130 may be operably coupled to an electrode trace 132 that may extend over a tether 105 to the center of the membrane 101. A first electrode 134 may be coupled to an electrode trace 132 and a second electrode 136 may be coupled to another electrode trace 132. The first electrode 134 and the second electrode 136 may comprise interdigitated electrodes 135. The electrode traces 132 may also be referred to herein as "chemical sensing electrode traces."

The first electrode 134 and the second electrode 136 may form one or more patterns and may be referred to herein as "interdigitated electrodes." As illustrated in FIG. 1B, the first electrode 134 may be in electrical contact with one of the bond pads 130 of the pair of bond pads 130 and the second electrode 136 may be in electrical contact with the other bond pad 130 of the pair of bond pads 130. The first electrode 134 may include protrusions 138 extending from a base thereof and may be received by gaps (e.g., spaces) between adjacent protrusions 140 extending from a base of the second electrode 136. The second electrode 136 may include protrusions 140 extending from the base thereof and may be received by gaps between adjacent protrusions 138 extending from the second electrode 136. In other embodiments, the first electrode 134 and the second electrode 136 may not include the protrusions 138, 140, respectively.

Accordingly, with reference to FIG. 1A and FIG. 1B, each tether 105 of the device 100 may include a conductive trace thereon. For example, two of the tethers 105 (e.g., the first tether 105a and the second tether 105b) may include the electrically conductive traces 115 thereon, two of the tethers 105 may include the sense lines 124 thereon, and two of the tethers 105 may include the electrode traces 132 thereon. In other embodiments, it is contemplated that at least some of the tethers 105 may not include a conductive trace thereon. By way of non-limiting example, in some embodiments, the device 100 may not include the sense lines 124, but may include the electrically conductive traces 115 and the electrode traces 132.

FIG. 1C is a side cross-sectional view of the device 100 taken along section line C-C (FIG. 1A). The cross-sectional view of the device 100 in FIG. 1C does not transverse any of the tethers 105. As illustrated, the void 104 may extend under the membrane 101 and separate the membrane 101 from the substrate 102.

In some embodiments, a thickness of the resistive heater 110 (e.g., a thickness in the vertical direction illustrated in FIG. 1C) may be between about 1,000 Å and about 4,000 Å, such as between about 1,500 Å and about 3,500 Å, or between about 2,000 Å and about 3,000 Å. However, the disclosure is not so limited and the thickness of the resistive heater 110 may be greater than or less than the thicknesses described above.

The membrane 101 and the tethers 105 may comprise a plurality of dielectric materials. A first dielectric material (e.g., an electrically insulating material) 160 may be disposed over and in contact with the substrate 102 at peripheral portions of the device 100 and extend over the void 104 to the membrane 101. The first dielectric material 160 may include silicon, a silicon oxide (e.g., silicon dioxide ($SiO_2$)), a nitride material (e.g., silicon nitride (e.g., $Si_3N_4$), hafnium nitride (e.g., $Hf_3N_4$), zirconium oxide (e.g., $Zr_3O_4$), or another insulating nitride material), a silicon carbide material, an oxynitride (e.g., silicon oxynitride (e.g., $Si_2N_2O$)), or combinations thereof. In some embodiments, the first dielectric material 160 comprises silicon dioxide. A thickness of the dielectric material 160 may be between about 100 Å and about 1,000 Å, such as between about 200 Å and about 800 Å, or between about 400 Å and about 600 Å. In some embodiments, the thickness of the dielectric material 160 is about 500 Å. However, the disclosure is not so limited and the thickness of the dielectric material 160 may be greater than or less than the thicknesses described above.

A second dielectric material (e.g., another electrically insulating material) 162 may overlie the first dielectric material 160. The second dielectric material 162 may directly overlie and contact the first dielectric material 160. The second dielectric material 162 may include silicon, a silicon oxide, a nitride material, a silicon carbide material, an oxynitride, or combinations thereof. In some embodiments, the second dielectric material 162 comprises a nitride material, such as a silicon nitride material. A thickness of the second dielectric material 162 may be between about 1,000 Å and about 6,000 Å, such as between about 2,000 Å and about 5,000 Å, or between about 3,000 Å and about 4,000 Å. However, the disclosure is not so limited and the thickness of the second dielectric material 162 may be greater than or less than the thicknesses described above. The second dielectric material 162 may be formed by one or more of atomic layer deposition (ALD), chemical vapor deposition (CVD), low pressure chemical vapor deposition (LPCVD), plasma-enhanced chemical vapor deposition (PECVD), or other deposition process. In some embodiments, the second dielectric material 162 is formed by LPCVD. Accordingly, in some such embodiments, the second dielectric material 162 may comprise a LPCVD nitride material.

With continued reference to FIG. 1C, the resistive heater 110 may overlie portions of the second dielectric material 162. A third dielectric material 164 may overlie and surround side surfaces of the resistive heater 110 at the membrane 101. The third dielectric material 164 may include one or more layers of silicon, silicon oxide (e.g., silicon dioxide), a silicon nitride (e.g., $Si_xN_y$) material, a silicon carbide material, an oxynitride, or combinations thereof. In some embodiments, the third dielectric material 164 comprises a silicon oxide (e.g., silicon dioxide) over a PECVD silicon nitride layer. In some embodiments, the third dielectric material 164 may be disposed in the gaps 120 (FIG. 1A) between adjacent portions (e.g., adjacent portions of the spiral) of the resistive heater 110. At the peripheral portions of the device 100, the third dielectric material 164 may directly overlie and contact the second dielectric material 162. A thickness of the third dielectric material 164 may be between about 1,000 Å and about 6,000 Å, such as between about 2,000 Å and about 5,000 Å, or between about 3,000 Å and about 4,000 Å. However, the disclosure is not so limited and the thickness of the third dielectric material 164 may be greater than or less than the thicknesses described above. The third dielectric material 164 may be formed by one or more of ALD, CVD, LPCVD, PECVD, or other deposition process. In some embodiments, the third dielectric material 164 is formed by PECVD. In some such embodiments, the third dielectric material 164 comprise a PECVD silicon oxide material.

Each of the first dielectric material 160, the second dielectric material 162, and the third dielectric material 164 may be selected to exhibit at least one of a different tensile stress or a compressive stress, which may be selected to have a magnitude between about 200 MPa and about 2 GPa at room temperature (e.g., about 25° C.). In some embodiments, the tethers 105, 105a, 105b, which may include one or more of the first dielectric material 160, the second dielectric material 162, and the third dielectric material 164 may exhibit a composite stress such that the membrane 101 is held in tension and remains substantially planar suspended over the void 104. The different stress values may be selected to balance a stress of the membrane 101 or the device 100 about a neutral axis of the stack of materials (e.g., the stack of materials comprising the membrane 101 (i.e., the first dielectric material 160, the second dielectric material 162, and the third dielectric material 164)), such as at operating temperatures (e.g., at temperatures between about 600° C. and about 1,200° C., such as between about 600° C. and about 800° C., between about 800° C. and about 1,000° C., or between about 1,000° C. and about 1,200° C.) of the device 100. Accordingly, the different materials and thickness of the tethers 105, 105a, 105b may be selected to achieve the desired stress (e.g., composite stress, compressive stress, tensile stress, etc.) and exhibit a desired tension on the membrane 101.

A thickness of each of the first dielectric material 160, the second dielectric material 162, and the third dielectric material 164 may be selected and tuned to exhibit an optimal residual tensile stress, which may result in a reduced mechanical deflection of the membrane 101 at operating temperatures thereof. In some embodiments, a formation temperature (e.g., a deposition temperature), a formation pressure (e.g., a deposition pressure), or both of one or more of the first dielectric material 160, the second dielectric material 162, and the third dielectric material 164 may be selected to tune a residual stress (e.g., a residual tensile stress) of one or more of the first dielectric material 160, the second dielectric material 162, and the third dielectric material 164. By way of non-limiting example, one or more of the first dielectric material 160, the second dielectric material 162, and the third dielectric material 164 may be formed (e.g., deposited) at a temperature between about 300° C. and about 700° C. In some embodiments, a residual stress of the membrane 101 may be tuned by controlling a deposition power at which one or more of the first dielectric material 160, the second dielectric material 162, and the third dielectric material 164 is deposited. A residual stress between layers of the membrane 101 may change responsive to heating and expansion of the materials (e.g., such as during operation of the resistive heater 110). Responsive to heating, the materials of the membrane 101 may exhibit a change in overall stress tensor (e.g., a reduction in the overall stress tensor). In some embodiments, the materials of the membrane 101 may be formed, formulated, and configured such that the stress does not become compressive during operation (e.g., at operating temperatures of the resistive heater 110). In some such embodiments, buckling or substantial out of plane motions (i.e., up and down in the view of FIG. 1C) of the membrane 101 may be reduced or even eliminated. Accordingly, tuning the residual tensile stress may reduce a likelihood of the membrane 101 from separating from the tethers 105.

In some embodiments, after the first dielectric material 160, the second dielectric material 162, and the third dielectric material 164 are formed, the stack of materials may be annealed. In some embodiments, the annealing may be performed at a temperature between about 400° C. and about 800° C., such as between about 500° C. and about 700° C. In some embodiments, the annealing is performed at a temperature of about 600° C. Annealing the materials may form the materials having a desired stress. After annealing, the materials may be patterned to form the void 104 in the substrate 102, such as by wet etching using, for example, a wet etchant. In some embodiments, the wet etchant may comprise potassium hydroxide (KOH), tetramethylammonium hydroxide (TMAH), calcium hydroxide (Ca(OH)$_2$), or other suitable caustic material. In some embodiments, the etching comprises isotropic etching. The etching may be performed from a back side of the substrate 102 (e.g., from a lower side of the substrate 102 illustrated in FIG. 1C), a front side of the substrate 102, of from both sides of the substrate 102. Etching may form the membrane 101 suspended above the substrate 102 by the tethers 105. In some embodiments, etching from the back side may facilitate forming the tethers 105 extending from the substrate 102 at a peripheral portion of the device 100 over the void 104 to the membrane 101.

As shown in FIG. 1C, taken by cross-section, an outermost portion of the resistive heater 110 may have a relatively smaller width (e.g., a distance from left to right in the cross-section illustrated in FIG. 1C) than portions of the resistive heater 110 proximate to the center of the membrane 101.

Figure 1D:
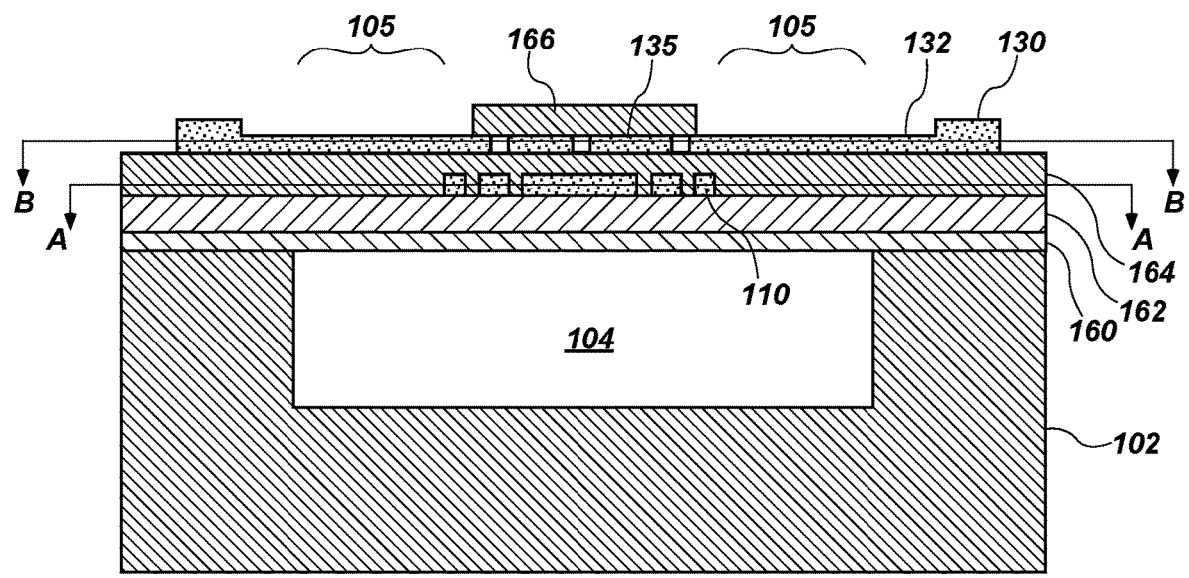
FIG. 1D is a side cross-sectional view of the microhotplate of FIG. 1A taken along section line D-D of FIG. 1A.

With continued reference to FIG. 1C, the interdigitated electrodes 135 (e.g., each of the first electrode 134 and the second electrode 136) may directly overlie and contact the third dielectric material 164 at the membrane 101. In some embodiments, a chemical sensing material 166 may directly overlie and contact the interdigitated electrodes 135. The chemical sensing material 166 may overlie and be disposed in between gaps of the interdigitated electrodes 135. The chemical sensing material 166 may be in electrical contact with the interdigitated electrodes 135 such that the electrical characteristics of the chemical sensing material 166 (e.g., a resistivity between the interdigitated electrodes due to the chemical sensing material 166) may be determined through the bond pads 130 (FIG. 1B, FIG. 1D). As used herein, the terms "resistivity" and "electrical resistance" are used interchangeably. The chemical sensing material 166 may comprise a material formulated and configured to exhibit a change in electrical resistance responsive to interaction with (e.g., reaction with, adsorption of, absorption of, oxidation by, reduction by, etc.) one or more chemicals (e.g., analytes) of interest, such as when an analyte is present thereon. In some embodiments, the chemical sensing material 166 may be formulated and configured to adsorb, absorb, or chemically react with at least one analyte of interest. The chemical sensing material 166 may also be referred to herein as a metal oxide semiconductor (MOS) coating ("MOS coating") and the device 100 may also be referred to herein as a "MOS microhotplate."

The chemical sensing material 166 may comprise a metal oxide (e.g., tin oxide, zinc oxide, tungsten oxide (e.g., WO$_3$), a manganese oxide (e.g., MnO, MnO$_2$, Mn$_2$O$_3$), LaCoO$_3$, LaNiO$_3$, vanadium oxide (e.g., V$_2$O$_5$), phosphorous pentoxide (e.g., P$_2$O$_5$), molybdenum oxide (MoO$_2$), cesium oxide (e.g., Cs$_2$O), etc.), a doped metal oxide (e.g., platinum-doped tin oxide), a polymer material (e.g., an electrically conductive polymer material), an ionic conductor (e.g., an electrochemical coating (also referred to as an e-chem coating)) material, an n-type semiconductor material, a p-type semiconductor material, a thermoelectric material, another material, or combinations thereof. In other embodiments, the chemical sensing material 166 comprises a semistor material formulated and configured to exhibit a change in one or more electrical properties responsive to reacting with an analyte. The semistor material may comprise, for example, tin oxide (e.g., SnO$_2$), titanium oxide (e.g., TiO$_2$), tungsten oxide (e.g., WO$_3$), yttria-stabilized zirconia (YSZ), or combinations thereof.

With continued reference to FIG. 1C, the membrane 101 may include the first dielectric material 160 suspended over the void 104, the second dielectric material 162 over the first dielectric material 160, and the resistive heater 110 over the second dielectric material 162. The third dielectric material 164 may overlie the second dielectric material 162 and the resistive heater 110 and may be disposed in the gaps 120 (FIG. 1A) of the resistive heater 110. The interdigitated electrodes 135 may overlie the third dielectric material 164 and the chemical sensing material 166 may overlie the interdigitated electrodes 135. At the periphery of the device 100, the first dielectric material 160 may overlie the substrate 102, the second dielectric material 162 may overlie the first dielectric material 160, and the third dielectric material 164 may overlie the second dielectric material 162. Accordingly, in some embodiments, the tethers 105, 105a, 105b may be formed of and comprise the same materials as the membrane 101.

FIG. 1D is a side cross-sectional view of the device 100 taken along the electrode trace 132 (FIG. 1B) and the tethers 105 (FIG. 1A) supporting the electrode trace 132. The interdigitated electrode 135 and the electrode trace 132 may be disposed over the third dielectric material 164 and above the resistive heater 110. The electrode trace 132 may be in electrical contact with the chemical sensing material 166 and may be configured to detect electrical properties (e.g., an electrical resistance) of the chemical sensing material 166.

Figure 1E:
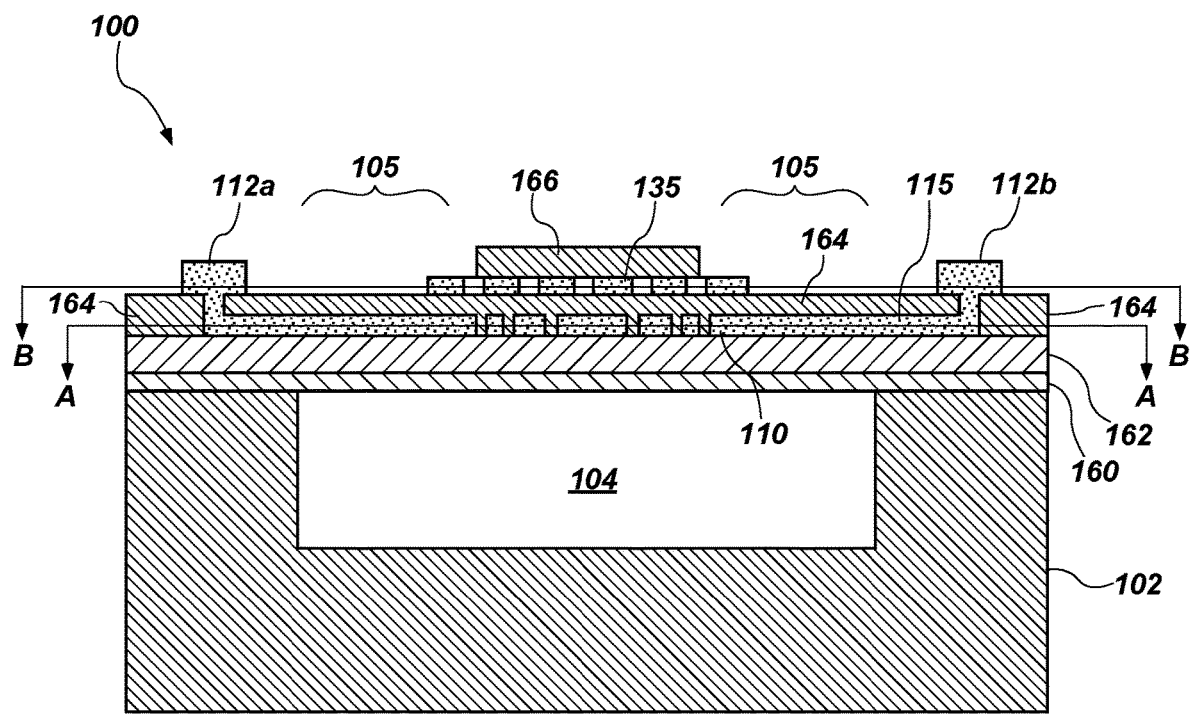
FIG. 1E is a side cross-sectional view of the microhotplate of FIG. 1A taken along section line E-E in FIG. 1A.
Figure 1F:
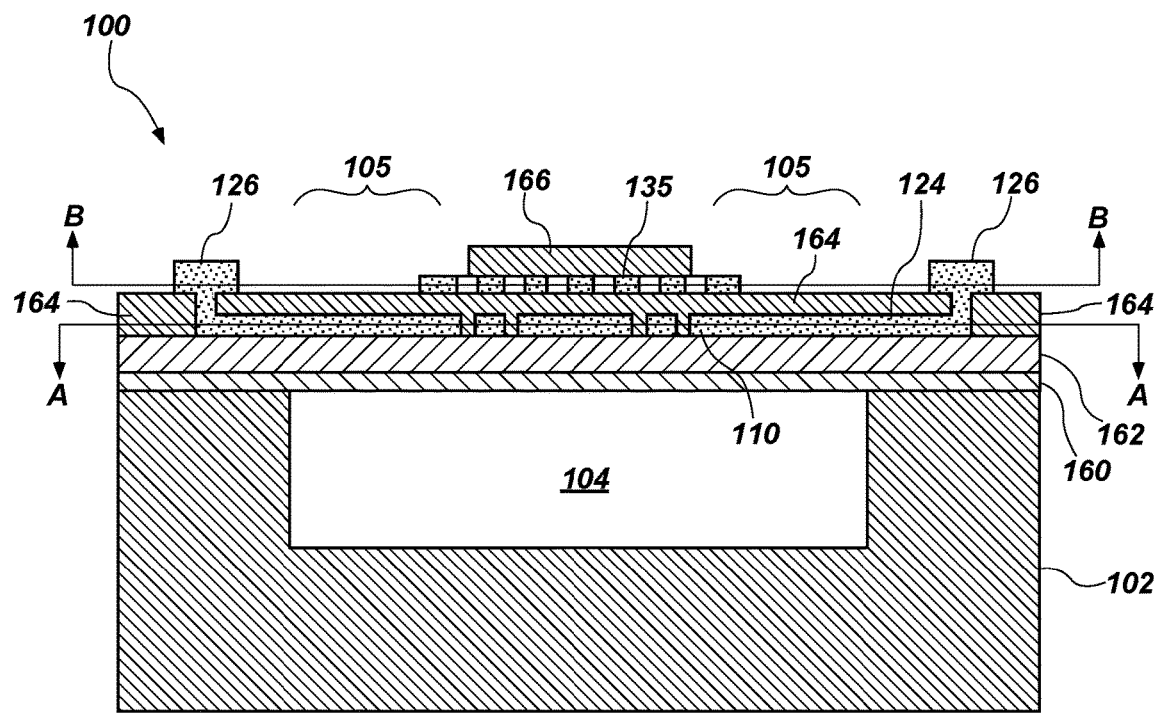
FIG. 1F is a side cross-sectional view of the microhotplate taken along section line F-F in FIG. 1A.

FIG. 1E is a side cross-sectional view of the device 100 taken along the electrically conductive trace 115 (FIG. 1A) and FIG. 1F is a side cross-sectional view of the device 100 taken along the sense lines 124 (FIG. 1A). As illustrated, the electrically conductive trace 115 and the sense lines 124 may be coplanar and may be in electrical contact with the resistive heater 110.

In some embodiments, forming one or more of the electrically conductive traces 115, the sense lines 124, and the electrode traces 132 to comprise a material exhibiting a low thermal conductivity (e.g., tungsten) relative to other conductive materials may reduce conductive thermal transfer and heat loss from the one or more of the electrically conductive traces 115, the sense lines 124, and the electrode traces 132 to the substrate 102 through the tethers 105, 105a, 105b. In addition, forming the tethers 105, 105a, 105b from one or more materials exhibiting a relatively low thermal conductivity (such as the first dielectric material 160, the second dielectric material 162, and the third dielectric material 164, each of which may comprise, for example, one or more of a nitride, an oxide, a low thermal conductivity ceramic material) may reduce conductive heat losses from the one or more of the electrically conductive traces 115, the sense lines 124, and the electrode traces 132 to the substrate 102 through the tethers 105, 105a, 105b. Forming the tethers 105, 105a, 105b to have a relatively thin width may further reduce conductive heat losses from the electrically conductive traces 115, the sense lines 124, and the electrode traces 132 to the substrate 102.

Figure 1G:
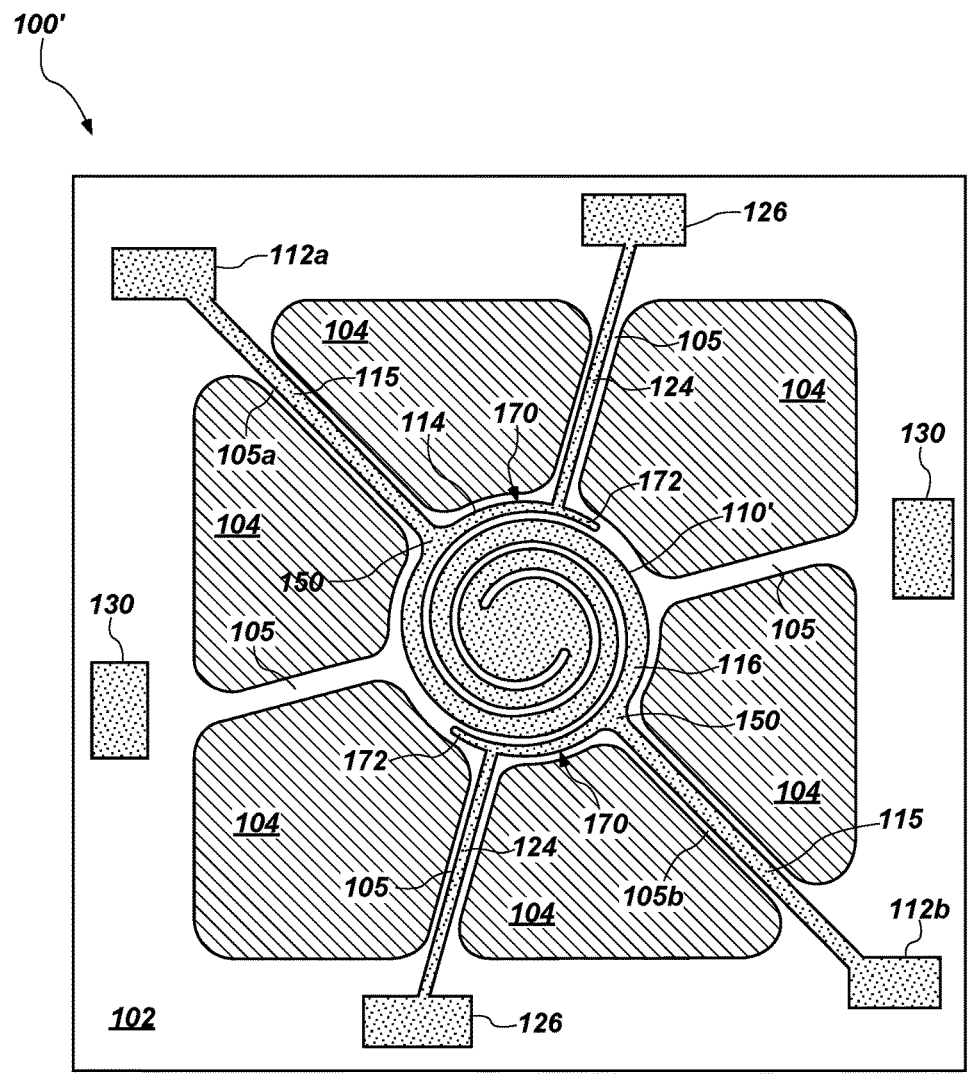
FIG. 1G is a top cross-sectional view of a microhotplate, in accordance with other embodiments of the disclosure.

Although the device 100 has been described and illustrated as including the resistive heater 110, the disclosure is not so limited. FIG. 1G is a top view of a device 100' comprising a microhotplate, in accordance with embodiments of the disclosure. The device 100' may be substantially similar to the device 100 described above with reference to FIG. 1A through FIG. 1F, except that the device 100' may include a resistive heater 110' different than the resistive heater 110 of FIG. 1A. The resistive heater 110' may be heated by application of a current between the first portion 114 and the second portion 116 applied through the electrically conductive traces 115, as described above with reference to FIG. 1A. The first portion 114 of the resistive heater 110' may include an extended portion 170 extending between the sense line 124 and the intersection of the tether 105a and the first portion 114. Similarly, the second portion 116 of the resistive heater 110' may include an extended portion 170 extending between the sense line 124 and the intersection of the tether 105b and the second portion 116. The first portion 114 and the second portion 116 may include a protrusion 172 extending beyond the intersection of the sense line 124 and the respective first portion 114 and second portion 116.

In some embodiments, electrically connecting the sense lines 124 to the resistive heater 110' at a location of the resistive heater 110' that is not in a current path between the bond pads 112a, 112b may facilitate improved sensitivity of the sense lines 124. It is believed that because substantially no current flows in the extended portions 170 (since the extended portions 170 are not located in a current path of the resistive heater 110' between the bond pads 112a, 112b), there is substantially no voltage drop in the extended portions 170. Accordingly, improved voltage measurements may be obtained with the sense lines 124 electrically coupled to the extended portions 170 of the resistive heater 110'.

In some embodiments, the protrusions 172 may reduce radiative and convective heat losses from the membrane 101 and may improve a temperature uniformity of the membrane 101. A width of the protrusions 172 may decrease with a distance from the widened portions 150.

Figure 2:
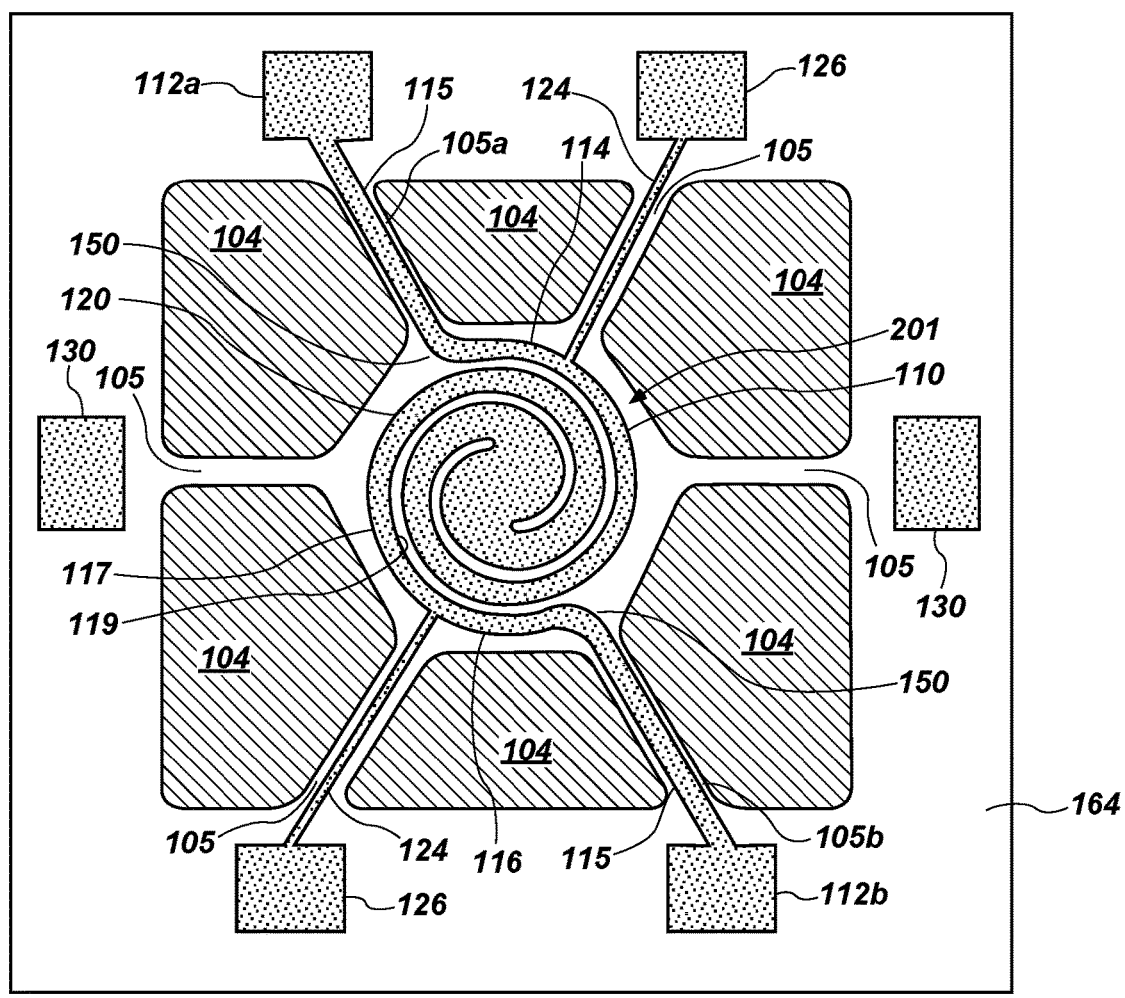
FIG. 2 is a top cross-sectional view of another microhotplate, in accordance with embodiments of the disclosure.

Although the device 100 has been described and illustrated as comprising a circular membrane 101, the disclosure is not so limited. In other embodiments, the membrane 101 may have a polygonal shape, such as a pentagonal shape, a hexagonal shape, a heptagonal shape, an octagonal shape, or other polygonal shape having a plurality of sides. In some embodiments, and as illustrated in FIG. 2, a device 200 may comprise a hexagonal membrane 201, as shown in the dotted lines.

Figure 3A:
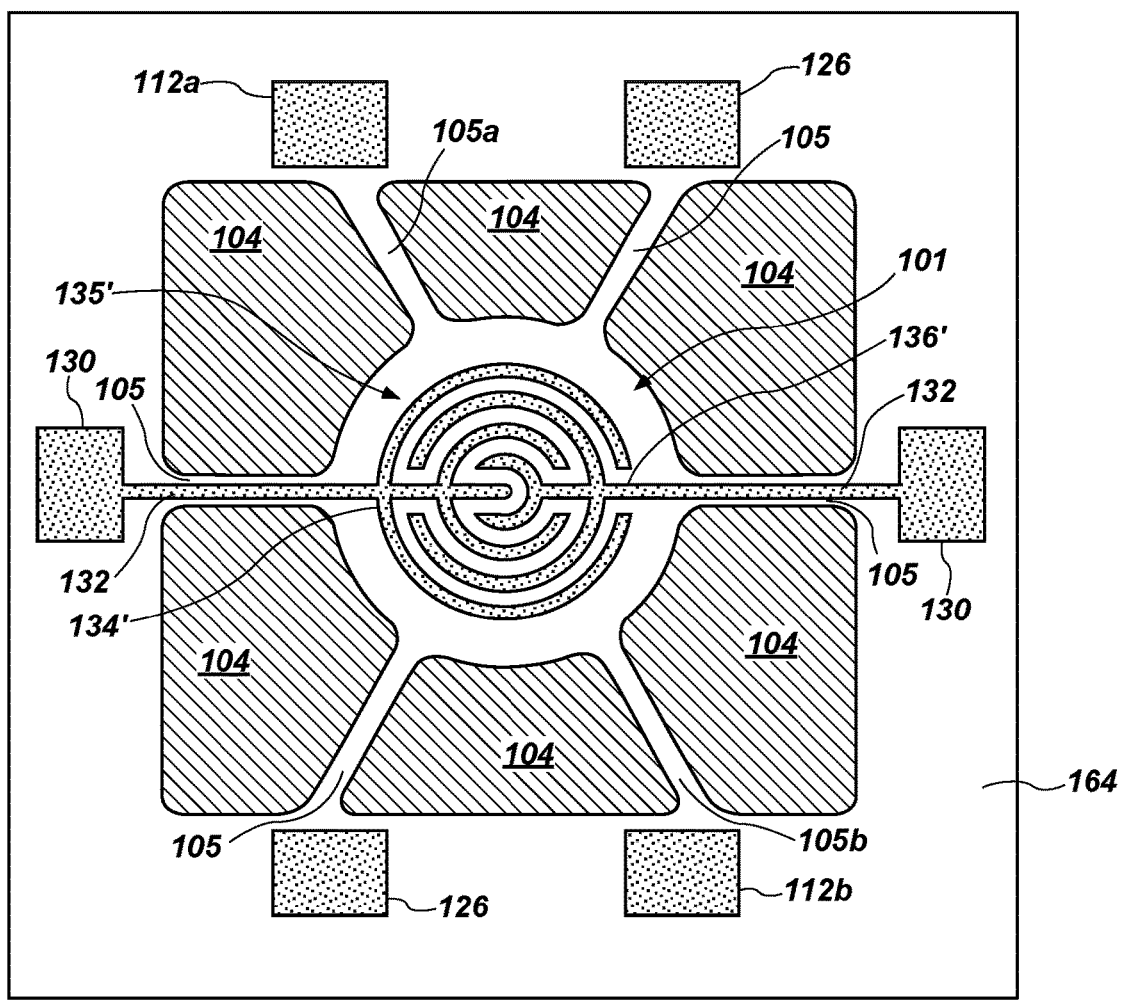
FIG. 3A is a top cross-sectional view of another microhotplate, in accordance with embodiments of the disclosure.

Although the device 100 has been described as comprising interdigitated electrodes 135 (FIG. 1B) having a particular shape, the disclosure is not so limited. FIG. 3A, is a cross-sectional view of another device 300 including interdigitated electrodes 135' comprising a first electrode 134' and a second electrode 136' having a different pattern than the interdigitated electrodes 135 of FIG. 1B. The first electrode 134' and the second electrode 136' may be shaped and configured to optimize a distance between the electrodes. In some embodiments, the distance between the first electrode 134' and the second electrode 136' may be selected depending on electrical characteristics of the material (e.g., the chemical sensing material 166) disposed over the interdigitated electrodes 135'.

The first electrode 134' may be in electrical contact with one of the bond pads 130 of the pair of bond pads 130 and the second electrode 136' may be in electrical contact with the other bond pad 130 of the pair of bond pads 130. The first electrode 134' and the second electrode 136' may comprise alternating concentric regions. By way of non-limiting example, an outermost portion of the first electrode 134' may be located further from the center of the membrane 101 than an outer portion of the second electrode 136'. The outer portion of the second electrode 136' may be adjacent the outer portion of the first electrode 134' and another portion of the first electrode 134'.

Figure 3B:
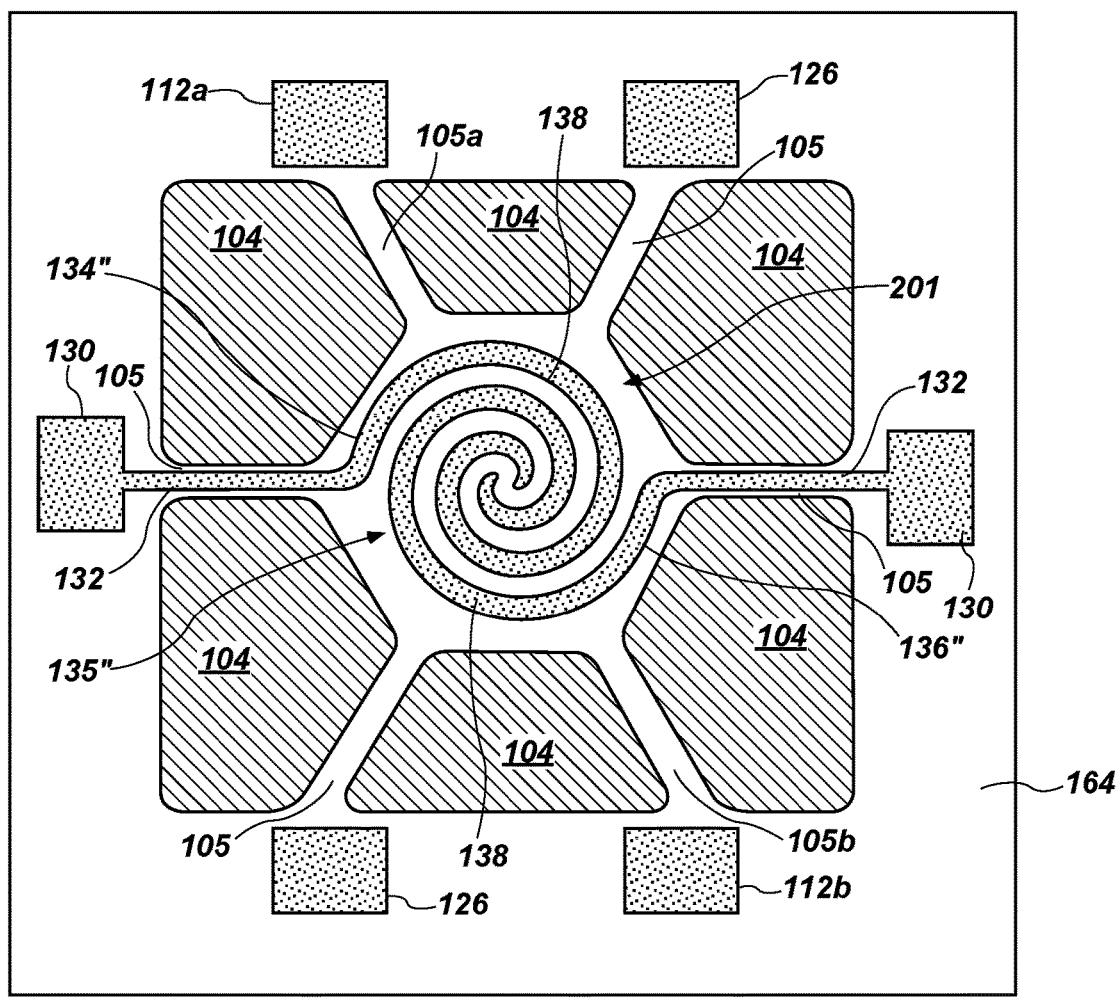
FIG. 3B is a top cross-sectional view of another microhotplate, in accordance with embodiments of the disclosure.

FIG. 3B is a cross-sectional view of another device 300' including interdigitated electrodes 135" comprising a first electrode 134" and a second electrode 136" having a different pattern than those illustrated in FIG. 1B and FIG. 3A. The first electrode 134" and the second electrode 136" may each have a spiral shape. The first electrode 134" may be in electrical contact with one bond pad 130 of the pair of bond pads 130 and the second electrode 136" may be in electrical contact with the other bond pad 130 of the pair of bond pads 130. The first electrode 134" may spiral in a first direction (e.g., one of a clockwise direction and a counterclockwise direction) and the second electrode 136" may spiral in a second direction (e.g., the other of the clockwise direction and the counterclockwise direction). In some embodiments, the spiral shape is substantially the same as the spiral shape of the resistive heater 110 (FIG. 1A), but the first electrode 134" and the second electrode 136" may have a substantially constant width along a length thereof. Accordingly, in some embodiments, the device 300' may include interdigitated electrodes 135" and a resistive heater exhibiting a spiral shape.

In some embodiments, the devices 100, 200, 300, 300' may include a heat spreader. The heat spreader may be disposed above or below one or more of the resistive heater 110 and may be isolated from the resistive heater 110 by one or more dielectric materials (e.g., one or more of the first dielectric material 160, the second dielectric material 162, or the third dielectric material 164). In some embodiments, the heat spreader may be disposed above the resistive heater 110 and below the interdigitated electrodes 135 (i.e., between the resistive heater 110 and the interdigitated electrodes 135). The heat spreader may improve the heat distribution (i.e., heat transfer) and temperature uniformity of the resistive heater 110 and the membrane 101.

In use and operation, a sensor including one or more of the devices 100, 200, 300, 300' may be used to determine one or more properties (e.g., a composition, a presence of at least one species, etc.) of an analyte. The resistive heater 110 may be heated to a predetermined temperature by applying a current to the resistive heater 110 through the electrically conductive traces 115. A temperature of the resistive heater 110 may be determined by measuring the voltage drop across the resistive heater 110 and determining the resistance according to Equation (2) below:

$$R = V/I \qquad (2),$$

wherein R is the resistance of the resistive heater 110, V is the voltage drop measured across the resistive heater, and I is the current provided to the resistive heater 110 through the electrically conductive traces 115. A temperature of the resistive heater 110 may be determined based on the resistance of the resistive heater 110, since a temperature of the resistive heater 110 may be proportional to the resistance thereof. In some embodiments, the voltage drop across the resistive heater 110 may be measured with the sense lines 124. In other embodiments, the voltage drop may be measured at a printed circuit board from which the current to the resistive heater 110 is provided. In some embodiments, measuring the voltage drop with the sense lines 124 may increase the accuracy of such measurements since measurement with the sense lines 124 reduces resistance losses due to wiring and other circuitry prior to obtaining a differential voltage measurement across the resistive heater 110. If sense lines 124 are not used, the accuracy of the measured resistance (which is proportional to the temperature) can be improved by compensating the measured resistance for the resistance of the interconnect wiring (i.e., the resistance from, for example, the printed circuit board to the bond pads 112a, 112b) and tether connection to the heater (i.e., the electrically conductive traces 115). In one embodiment, the compensation may be accomplished by measuring a total resistance from the current source and across the resistive heater 110 (which total resistance may account for the resistance of the bond pads 112a, 112b, the resistance of the electrically conductive traces 115, the resistance of the resistive heater 110, and the resistance of any bonding wires and/or interconnect structures between the current source and the bond pads 112a, 112b). In other embodiments, the compensation may be accomplished by applying a mathematical formula. An example of such a compensation formula is given below in Equation (3):

$$R_{comp}=R_{target}(1+B(T_{amb}-T_o)) \quad (3),$$

wherein $R_{comp}$ is the compensated resistance value, $R_{target}$ is the measured resistance from the total power applied to the resistive heater 110, B is the compensation factor (° C./° C.) that may be unique for a given device 100 and membrane 101 of particular dimension and materials (i.e., the value of B may be constant and unique for particular dimensions and materials of the microhotplate), $T_{amb}$ is the current ambient temperature as measured from an environmental sensor (or measurement of the ambient resistance of the microhotplate), and $T_o$ is a calibration temperature.

In other embodiments, the resistance measured across the resistive heater 110 may be compensated using a reference microhotplate. In some such embodiments, the reference microhotplate may include sense lines (e.g., sense lines 124). The sense lines of the reference microhotplate may be used to set a temperature of the device 100 to a desired temperature, such as by adjusting the current through the resistive heater until the resistance of the resistive heater is at a value that corresponds to the desired temperature. The current and voltage to the microhotplate device 100 without sense lines 124 may be set to the same values as the current and voltage applied to the resistive heater of the reference microhotplate, thus achieving the same temperature of the resistive heater 110 of the device 100 as the temperature of the reference microhotplate with the sense lines.

A resistance (i.e., an electrical conductivity) of the chemical sensing material 166 may be measured at the bond pads 130. The resistance of the chemical sensing material 166 may be a function of interactions of an analyte with the chemical sensing material 166. Stated another way, an electrical resistance of the chemical sensing material 166 may change when it interacts with one or more species in an analyte. In some embodiments, the chemical sensing material 166 may be formulated and configured to interact with particular species (e.g., gases).

In some embodiments, the electrical conductivity of the chemical sensing material 166 may be measured at a plurality of temperatures to determine a presence of a particular species (e.g., a gas) in an analyte. The response (e.g., the electrical conductivity) of the chemical sensing material 166 may vary with temperature and the temperature profile may be used to determine a composition of an analyte or the presence of one or more gases in the analyte. In some embodiments, a sensor may include a plurality of devices 100, 200, 300, 300', each including a chemical sensing material 166 comprising a different composition and formulated and configured to interact with different species. The sensor may be used to determine the presence of one or more species in the analyte to which the devices 100, 200, 300, 300' are exposed.

Figure 4A:
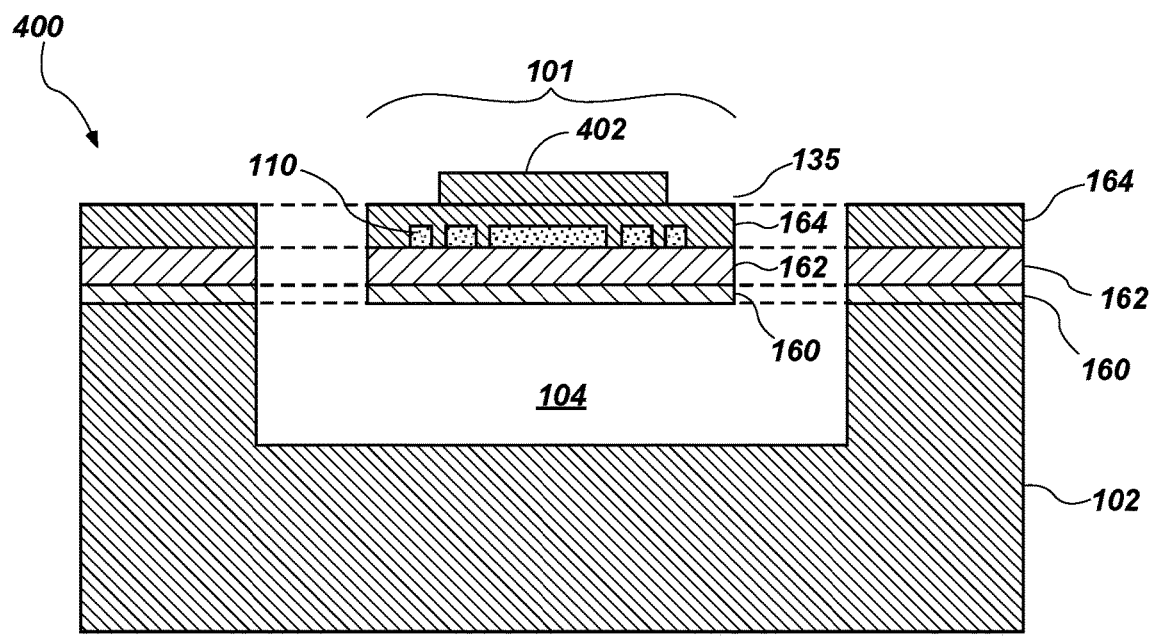
FIG. 4A and FIG. 4B are side cross-sectional views of another microhotplate, in accordance with embodiments of the disclosure.
Figure 4B:
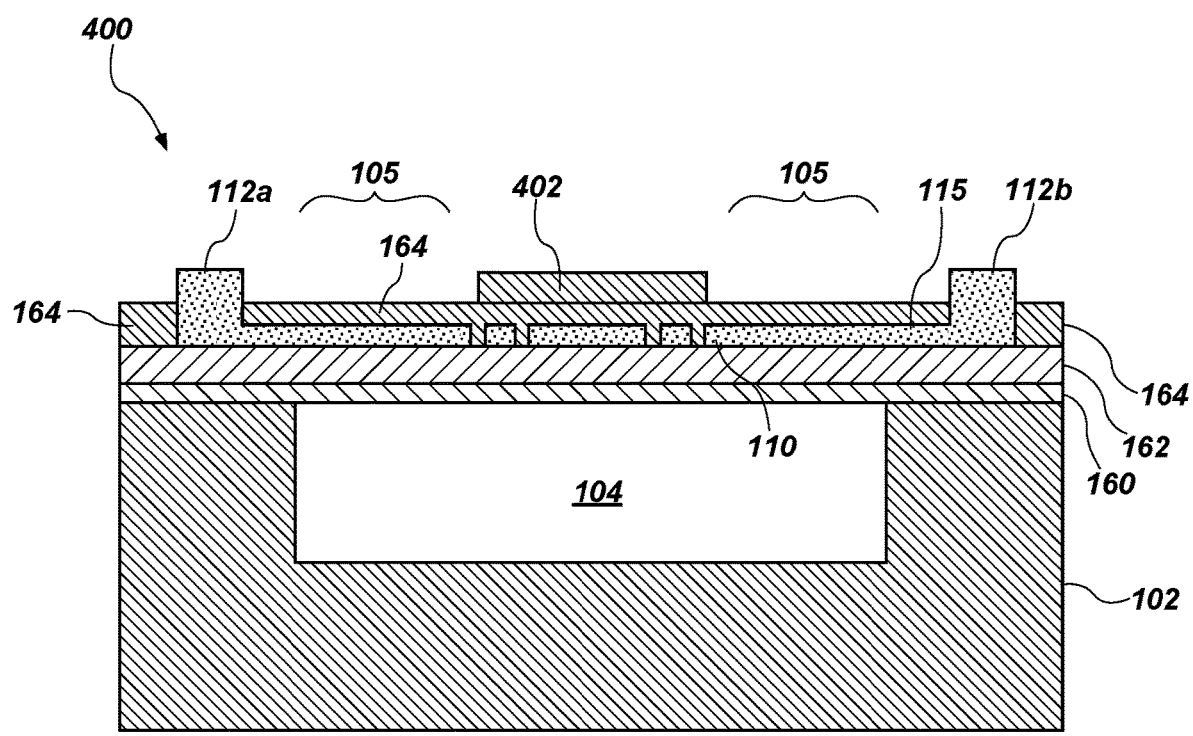

In some embodiments, the device 100 may not include the interdigitated electrodes 135. FIG. 4A and FIG. 4B are cross-sectional views of a device 400 according to other embodiments of the disclosure. The device 400 may be substantially the same as the devices 100, 200, 300, 300' described above, but may not include the chemical sensing material 166 (FIG. 1D). Accordingly, the device 400 may include a membrane 101 suspended over a substrate 102, which may comprise silicon. The membrane 101 may be suspended over the substrate 102 by a plurality of tethers 105, as described above with reference to FIG. 1A. The electrically conductive traces 115 may electrically connect the resistive heater 110 to the bond pads 112a, 112b and may extend over the tethers 105, as described above with reference to FIG. 1A and FIG. 1E. Accordingly, the resistive heater 110 may be powered by application of a current between the bond pads 112a, 112b.

Although not shown in FIG. 4A and FIG. 4B, the device 400 may include sense lines 124 in communication with the resistive heater 110, as described above with reference to FIG. 1A and FIG. 1G, for example. A voltage drop across the resistive heater 110 may be measured with sense lines 124 in electrical communication with the resistive heater 110 and with sense line bond pads 126, as described above with reference to FIG. 1A and FIG. 1F. Use of the sense lines 124 and sense line bond pads 126 may increase the sensitivity and accuracy with which the voltage drop across the resistive heater 110 may be measured. In other embodiments, the voltage drop across the resistive heater 110 may be measured without the sense lines or with sense lines and bond pads located elsewhere in the device 400.

The device 400 may include a coating material 402 and may comprise a catalytic microhotplate or a reference microhotplate, depending on a composition of the coating material 402. As used herein, the term "catalytic microhotplate" means and includes a device including a resistive heater, sense lines (e.g., sense lines 124) in electrical communication with the resistive heater, and a coating material 402 comprising a catalytically active material over a dielectric material overlying the resistive heater 110. As used herein, the term "reference microhotplate" means and includes a device including a resistive heater, sense lines (e.g., sense lines 124) in electrical communication with the resistive heater 110, and either no coating material or a chemically inert coating material over a dielectric material overlying the resistive heater. Accordingly, the reference microhotplate may be free of a coating material over the resistive heater 110 or may include a coating material 402 comprising an inert material over a dielectric material overlying the resistive heater.

The coating material 402 may be electrically isolated from the resistive heater 110 by one or more dielectric materials. By way of non-limiting example, the coating material 402 may directly overlie and contact the third dielectric material 164. In other embodiments, the coating material 402 may directly overlie and contact another dielectric material (e.g., the first dielectric material 160 or the second dielectric material 162). The coating material 402 may comprise an inert material (e.g., a reference material) or a catalyst material formulated and configured to catalyze, for example, an oxidation reaction and produce heat in the presence of predetermined analytes. The inert coating material may be configured and formulated to exhibit at least one of substantially a same mass (e.g., thermal mass), emissivity, convective heat loss, thermal conductivity, and surface area of a coating material comprising the catalyst material.

In some embodiments, the inert coating material comprises aluminum oxide (e.g., $Al_2O_3$). In some embodiments, such as where the coating material comprises a catalytic coating material, the catalyst material comprises palladium, platinum, ruthenium, silver, iridium, another catalyst metal, or combinations thereof. In some embodiments, the catalyst material may exhibit a relatively high porosity and may exhibit a high surface roughness, which may increase a total surface area of the catalyst material.

In some embodiments, a sensor system may comprise a device 400 having a coating material 402 comprising a catalyst material as a catalytic microhotplate and another device 400 comprising an inert coating material as a reference microhotplate. In some embodiments, the devices 400 may be formed in the same substrate. Stated another way, a sensor system may include at least one catalytic microhotplate and at least one reference microhotplate fabricated on the same substrate and may have identical features, except that the coating material 402 of the catalytic microhotplate may comprise a catalyst material and the reference microhotplate may comprise an inert coating material or may not include a coating material. As will be described herein, the system may be useful for measuring a catalytic heat of combustion or oxidation (such as with the catalytic microhotplate), or for directly measuring a thermal conductivity of a material (such as with the reference microhotplate), or both. In some embodiments, the device 400 comprising the inert coating material or not including the coating material may comprise a reference microhotplate. In some embodiments, the sensor system may further comprise a microhotplate comprising a chemical sensing material 166 (e.g., device 100 (FIG. 1A), and may comprise a MOS microhotplate).

In embodiments where the device 400 comprises a catalytic microhotplate (e.g., where the coating material 402 comprises a catalytic coating), the device 400 may be used to determine at least one of an exothermic event, an endothermic event, an onset of such events, or an ignition temperature of an analyte. In some embodiments, an exothermic event or an endothermic event may be detected by measuring a power required to achieve a given temperature. By way of non-limiting example, a temperature of the resistive heater 110 of the catalytic microhotplate may be ramped according to predetermined temperature steps by changing (e.g., ramping) a current provided to the resistive heater 110 through the electrically conductive traces 115. A voltage drop across the resistive heater 110 may be measured at each temperature while the temperature is changed (e.g., during the temperature ramp), such as by using the sense lines in electrical communication with the resistive heater 110. A power to achieve each temperature may be determined from the measured voltage drop at each temperature and the current provided at each temperature, according to Equation (4) below:

$$P = I * V \quad (4),$$

wherein P is the power, I is the current provided to the resistive heater 110, and V is the measured voltage drop across the sense lines. At a temperature between about 150° C. and about 250° C., any physiosorbed species (e.g., species that have been physically adsorbed to the catalytic coating) may be desorbed from the surface of the catalytic coating material 402 prior to ramping a temperature of the resistive heater 110 to greater temperatures where poisoning of the catalytic coating material 402 by undesired chemical reactions may occur. Accordingly, the catalytic coating material 402 may be preserved by ramping the temperature of the device 400 to a first lower temperature, followed by ramping the temperature to at least a second, higher temperature.

Baseline data (e.g., a current, a resistance, and a power required to maintain each temperature) may be stored in a memory associated with the catalytic microhotplate. The baseline data may include historical power versus temperature data from previous catalytic sensor temperature ramps. The baseline data may be subtracted from the current data to obtain a signal representative of changes in the catalytic microhotplate thermal response, according to Equation (5) below:

$$\text{Delta Cat} = \text{Cat}(n) - \text{Cat(baseline)} \quad (5),$$

wherein Delta Cat is the relative change in the catalytic microhotplate thermal response, Cat(n) is the thermal response of the current temperature ramp (e.g., the power required to maintain a predetermined temperature), and Cat(baseline) is the baseline data. The Cat(baseline) may comprise a historic average value of the power required to maintain each temperature of the resistive heater 110 and may be continuously updated during each temperature ramp. The Delta Cat value may be determined at each temperature during the temperature ramp. Accordingly, Delta Cat may correspond to a difference in power required to maintain a given temperature of the catalytic microhotplate compared to previous temperature ramps. In some embodiments, a Delta Cat value that deviates from zero may be an indication of a reaction on the catalytic microhotplate, an ignition temperature of an analyte in contact with the catalytic microhotplate, or both.

With continued reference to FIG. 4A and FIG. 4B, a reference microhotplate may comprise a device wherein the coating material 402 comprises an inert coating material. In other embodiments, the reference microhotplate may not include a coating material, as described above. The reference microhotplate may be fabricated on the same wafer (e.g., the same silicon wafer) as the catalytic microhotplate sensor. A temperature of the reference microhotplate may be changed (e.g., ramped) according to a same temperature changes (e.g., ramp) as the catalytic microhotplate. In some embodiments, the reference microhotplate and the catalytic microhotplate are exposed to a temperature ramp simultaneously. In some such embodiments, measurements from the catalytic microhotplate and measurements from the reference microhotplate may be correlated in time, may be exposed to substantially the same analyte, and may exhibit improved sensor accuracy.

Baseline data (e.g., a current, a resistance, and a power required to maintain each temperature) may be stored in a memory associated with the reference microhotplate. The baseline data may include historical power versus temperature data from previous reference microhotplate temperature changes (e.g., ramps). The baseline data may be subtracted from the current data to obtain a signal representative of changes in the reference microhotplate thermal response, according to Equation (6) below:

$$\text{Delta Ref} = \text{Ref}(n) - \text{Ref(baseline)} \quad (6),$$

wherein Delta Ref is the relative change in the reference microhotplate thermal response, Ref(n) is the thermal response of the current temperature (e.g., current temperature ramp), and Ref(baseline) is the baseline data (e.g., an average of Ref(n) data from previous temperature changes (ramps)). The Delta Ref value may be determined at each temperature (such as during the temperature ramp). The Delta Ref value may be an indication of the thermal conductivity of an analyte in contact with or proximate to the reference microhotplate. For example, a Delta Ref value that is greater than zero may be an indication that the thermal conductivity of the analyte is greater than a thermal conductivity of gases to which the reference microhotplate was exposed (e.g., air) during calibration or in previous ramps. Similarly, a Delta Ref value that is less than zero may be an indication that the thermal conductivity of the analyte is less than a thermal conductivity of gases to which the reference microhotplate was exposed in previous ramps. In some such embodiments, a thermal conductivity of the analyte may be determined according to differential thermal analysis (DTA) or differential scanning calorimetry (DCS) techniques. The thermal conductivity of a species or an analyte may be a function of temperature. Accordingly, in some embodiments, the thermal conductivity of an analyte may be determined at more than one temperature.

In other embodiments, a current provided to the resistive heater may be maintained and a resistance of the resistive heater may be measured with the sense lines to determine a temperature of the resistive heater. A thermal conductivity of the analyte may be determined based on the determined temperature for the power provided to the resistive heater. In some such embodiments, the thermal conductivity may be determined according to differential scanning calorimetry (DSC).

In some embodiments, the thermal conductivity may be measured at two or more temperatures. By way of non-limiting example, the thermal conductivity may be measured at relatively low temperatures (e.g., between about 50° C. and about 250° C.) and at relatively high temperatures (e.g., between about 400° C. and about 1,000° C.). Thermal conductivity generally increases with increasing temperatures. Therefore, Delta Ref measurements made at higher temperatures may exhibit a larger sensor response from the reference microhotplate, and may, therefore, increase the sensitivity of the reference microhotplate.

The Delta Ref signal may be subtracted from the Delta Cat signal to produce a signal response that is proportional to the heat generated on or removed from the catalytic sensor, according to Equation (7) below:

$$\text{Exo(new)} = \text{Delta Cat} - \text{Delta Ref} \quad (7),$$

wherein Exo(new) is the signal response that is proportional to the heat generated on or removed from the catalytic microhotplate and Delta Cat and Delta Ref are as previously described. Subtracting the Delta Ref signal from the Delta Cat signal may compensate the Delta Cat signal for the effects of thermal conductivity, thermal diffusivity, density, viscosity, temperature, pressure, relative humidity, flow variations, and other noise in the system and in the analyte being detected.

If the value of Exo(new) deviates from its nominal value, one or more of an exothermic reaction, an endothermic reaction, or an ignition of such reactions, which may also be referred to herein as a "light-off" event, may be detected. By way of example only, an Exo(new) value that is less than zero may be an indication of less power required to maintain a temperature of the catalytic microhotplate, which may be an indication of an exothermic reaction. Similarly, an Exo (new) value that is greater than zero may be an indication of more power required to maintain the temperature of the catalytic microhotplate, which may be an indication of an endothermic reaction.

The temperature of the light-off event may be an indication of a presence of a gas in the sample being detected. Since different gases catalytically oxidize at different temperatures, the light-off temperature of an analyte may be an indication of a presence of one or more gases in the analyte. Multiple light-off events at different temperatures may be an indication of multiple flammable gases present in the sample. A database may store the sensor responses, training data, and calibration data used in the analysis.

Although the devices 100, 200, 300, 300', 400 include a conductive trace (e.g., the electrically conductive trace 115, the sense lines 124, and the electrode trace 132), over each tether 105, in some embodiments, at least some of the tethers 105 may not include a conductive trace extending thereon.

Figure 5:
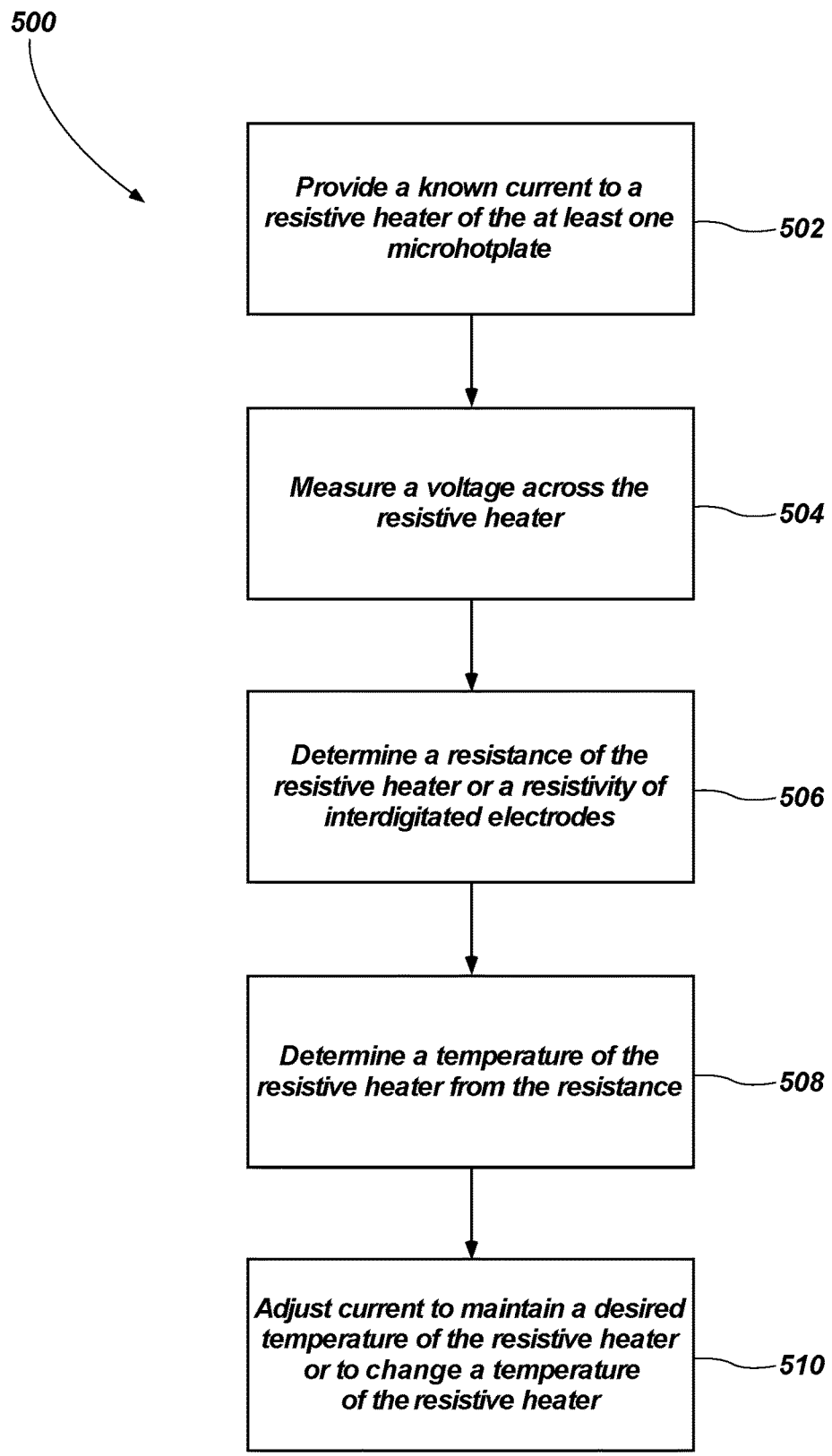
FIG. 5 is a flowchart illustrating a method of operating a gas sensor including at least one microhotplate, in accordance with embodiments of the disclosure.

In use and operation, the devices 100, 200, 300, 300', 400 may be used for sensing one or more gases, one or more properties of one or more gases, or a combination thereof. FIG. 5 is a flowchart illustrating a method 500 of operating a device including at least one microhotplate according to embodiments of the disclosure. The device may include one of at least one device 100, 200, 300, 300', 400 described above. By way of non-limiting example, the device may include at least one MOS microhotplate (e.g., at least one device 100, 200, 300, 300' as described above with reference to FIG. 1A through FIG. 1G, FIG. 2, FIG. 3A, and FIG. 3B), at least one reference microhotplate device (e.g., at least one device 400 including an inert coating material 402, or no coating material, as described above with reference to FIG. 4A and FIG. 4B), and at least one catalytic microhotplate (e.g., at least another device 400 including a catalytic coating material 402 as described above with reference to FIG. 4A and FIG. 4B).

The method 500 may include act 502 including providing a known current to a resistive heater of at least one microhotplate through electrically conductive traces; act 504 including measuring a voltage drop across the resistive heater with voltage sense lines; act 506 including determining a resistance of the resistive heater and optionally determining a resistivity between interdigitated electrodes; act 508 including determining a temperature of the resistive heater; and act 510 including adjusting the current to maintain a desired temperature of the resistive heater or to change a temperature of the resistive heater.

Act 502 includes providing a known current to a resistive heater of at least one microhotplate through conductive traces in electrical contact with the resistive heater. The current may raise a temperature of the resistive heater to a desired temperature. In some embodiments, the current is supplied in a stepped manner to raise the temperature of the resistive heater in a stepped manner. In some embodiments, the current is provided to the resistive heater to maintain a predetermined temperature of the resistive heater. In some embodiments, act 502 includes providing a current to a resistive heater of at least one MOS microhotplate, a resistive heater of at least one reference microhotplate, and a resistive heater of at least one catalytic microhotplate.

Act 504 includes measuring a voltage (e.g., a voltage drop) across the resistive heater. In some embodiments, the voltage drop across the resistive heater may be measured with voltage sense lines (e.g., sense lines 124 (FIG. 1A)) in electrical contact with the resistive heater. In other embodiments, the voltage drop may be measured without the sense lines. In other words, act 504 may include at least one of measuring a voltage drop across the resistive heater of at least one reference microhotplate, measuring a voltage drop across the resistive heater of at least one catalytic microhotplate, and measuring a voltage drop across a resistive heater of at least one MOS microhotplate. By way of non-limiting example, where the microhotplate device comprises a catalytic microhotplate or a reference microhotplate, act 504 may include measuring a voltage drop across sense lines in electrical contact with the resistive heater. Where the microhotplate device comprises a MOS microhotplate, act 504 may include measuring the voltage drop across the resistive heater at a location proximate where the current to the resistive heater is supplied (e.g., such as at a printed circuit board). In some embodiments, act 504 includes measuring a voltage drop across the resistive heater of at least one reference microhotplate, measuring a voltage drop across the resistive heater of at least one catalytic microhotplate, and measuring a voltage drop across the resistive heater of at least one MOS microhotplate.

Act 506 includes determining a resistance of the resistive heater and optionally determining a resistivity between the interdigitated electrodes. The resistivity between the interdigitated electrodes may correspond to the resistivity of the MOS coating of a MOS microhotplate. In some embodiments, act 506 includes determining a resistance of the resistive heater of one or more of at least one catalytic microhotplate, at least one reference microhotplate, and the resistive heater of at least one MOS microhotplate. The resistance of the resistive heater may be determined, based at least in part, on the current provided to the resistive heater and the voltage measured by the sense lines or elsewhere in the device. The resistance may be proportional to the measured voltage divided by the provided current (i.e., Ohms law, $R=V/I$, wherein R is the resistance, V is the measured voltage, and I is the provided current). In embodiments, where act 506 includes determining a resistivity between the interdigitated electrodes, the resistivity may be determined based on the measured voltage drop across interdigitated electrodes (e.g., across the electrode traces 132 (FIG. 1B)). The resistance of the interdigitated electrodes may be determined based on Ohms law, as described above with reference to the resistance of the resistive heater. In some embodiments, the resistivity between the interdigitated electrodes may be determined by providing a current to the interdigitated electrodes and measuring a voltage drop across the interdigitated electrodes. In other embodiments, the resistivity of the interdigitated electrodes may be determined by providing a voltage to the interdigitated electrodes and measuring a current through the interdigitated electrodes.

Act 508 includes determining a temperature of the resistive heater based, at least in part, on the determined resistance of the resistive heater. For example, the temperature of the resistive heater may be proportional to the resistance thereof according to, for example, the temperature coefficient of resistance of the resistive heater (e.g., $dR/R=\alpha \, dT/dR$, wherein R is the resistance of the resistive heater, dR is the change in resistance between a baseline resistance and a resistance of the resistive heater to exposure to a sample, dT is a difference in temperature between a baseline temperature and a temperature of the resistive heater to exposure to the sample, and $\alpha$ is a coefficient of thermal resistance of the resistive heater). Accordingly, the resistance may be used to determine the temperature of the resistive heater.

Act 510 includes adjusting the current to maintain a desired temperature of the resistive heater or to change (e.g., ramp) a temperature of the resistive heater. In some embodiments, the current may be adjusted in a stepped manner to change the temperature of the resistive heater in a corresponding stepped manner. A power required to maintain the temperature at each step may be determined based on the measured voltage drop across the resistive heater in act 506 and the current provided to the resistive heater in act 502 for each particular temperature. In other embodiments, the current provided to the resistive heater may be maintained at a substantially constant value to facilitate maintaining the temperature of the resistive heater at a substantially constant temperature. A power required to maintain the substantially constant temperature may be determined based on the measured voltage drop across the resistive heater in act 506 and the current provided to the resistive heater in act 502.

Although FIG. 5 has been described as including determining a resistance of the resistive heater by applying a current to the resistive heater and measuring a voltage drop across the resistive heater, the disclosure is not so limited. In other embodiments, a voltage may be applied to the resistive heater and a current through the resistive heater may be measured. The provided voltage and measured current may be used to determine the resistance.

In some embodiments, a power required to maintain a temperature of the resistive heater may be determined. The power may be related to the provided current and the measured voltage (e.g., $P=IV$, as described above with reference to Equation (4)). In other embodiments, the power may be related to the provided current and the resistance (e.g., $P=I^2R$). In some embodiments, the power required to maintain a predetermined temperature may be a function of the composition of the vapor being analyzed. In some embodiments, and as described above, a lower power required to maintain a desired temperature of the catalytic microhotplate may be an indication of an exothermic reaction occurring at the catalytic microhotplate. Similarly, a greater power required to maintain a desired temperature of the catalytic microhotplate may be an indication of an endothermic reaction occurring at the catalytic microhotplate. In some embodiments, use of the sense lines 124 (FIG. 1A) may facilitate an increased system resolution and accuracy of reference microhotplates and catalytic microhotplates. By way of non-limiting example, the sense lines 124 may facilitate determining powers as low as about 10 microWatts, or even as low as 1.0 microWatt, such as a power between about 1.0 microWatt and about 10 microWatts. Where the microhotplate comprises a reference microhotplate, a greater power required to achieve a given temperature may correlate to a gas having a higher thermal conductivity proximate the reference microhotplate. Similarly, a lower power required to achieve a given temperature may correlate to a gas having a lower thermal conductivity proximate the reference microhotplate. The thermal conductivity of the analyte may be determined based on the power required to maintain one or more temperatures.

Figure 6:
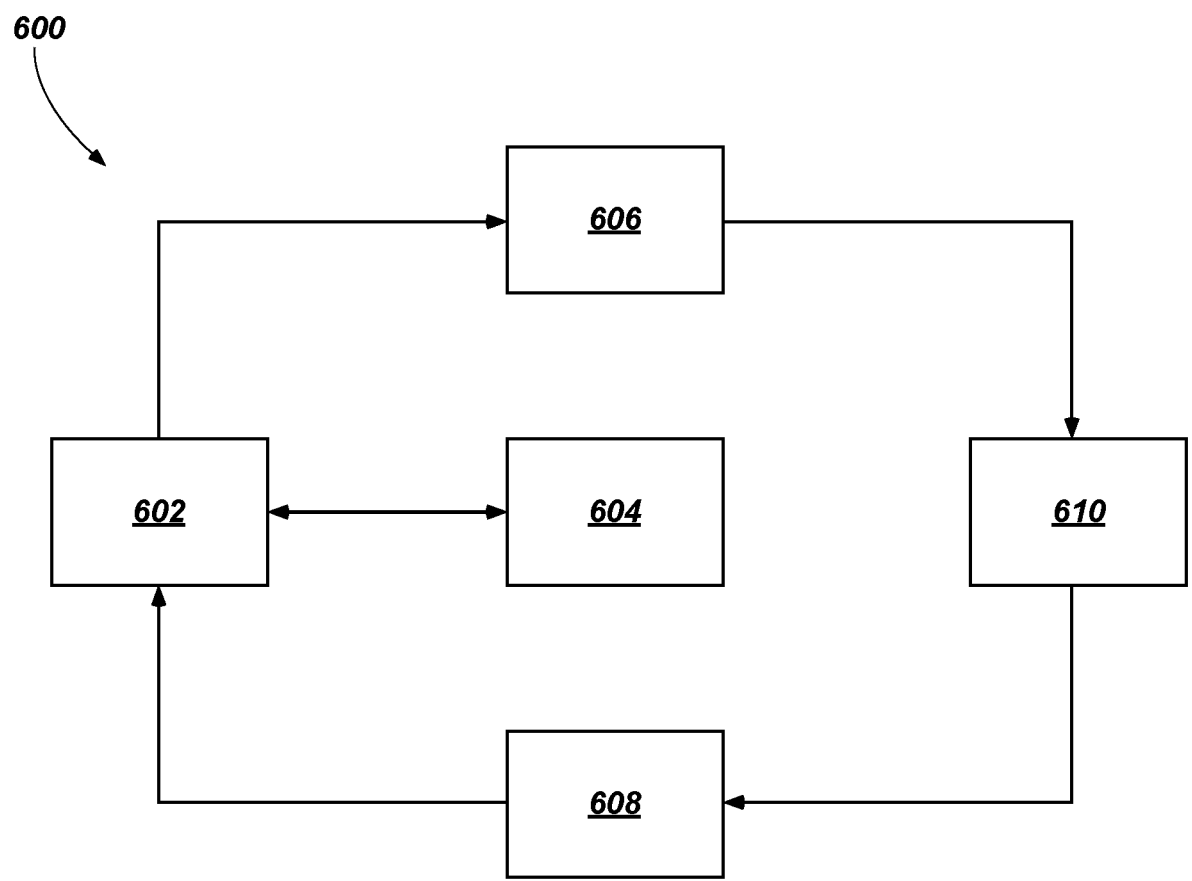
FIG. 6 is a simplified block diagram showing a computing system configured for carrying out one or more embodiments described herein.

FIG. 6 is a simplified block diagram of a system 600 configured for carrying out one or more embodiments of the present disclosure. The system 600 is configured for executing programs containing computing instructions and may include one or more processors 602, one or more memory devices 604, one or more driver circuits 606 for driving one or more resistive heaters of one or more devices, one or more sensors 608 for sensing one or more outputs of the one or more microhotplates (e.g., an output from a resistive heater, such as may be measured with sense lines, an output from an interdigitated electrode, such as may be measured with electrode traces, etc.), and an element 610, which may comprise a resistive heater for heating a microhotplate associated with the resistive heater, interdigitated electrodes, or both.

The one or more processors 602 may be configured for executing a wide variety of operating systems and applications including the computing instructions for carrying out embodiments of the present disclosure. The one or more processors 602 may be in communication with each of the one or more memory devices 604, the one or more driver circuits 606, and the one or more sensors 608. The one or more processors 602 may be configured to transmit operating instructions to the one or more driver circuits 606. By way of non-limiting example, the one or more processors 602 may be configured to provide operating instructions, such as instructions to provide a current, to the one or more driver circuits 606, which may drive a resistive heater associated with each device associated with the sensors 608. As only one example, the one or more processors 602 may be configured to provide operating instructions to the one or more driver circuits 606 to maintain a desired temperature of resistive heaters or to ramp a temperature of one or more resistive heaters associated with the one or more driver circuits 606.

The one or more driver circuits 606 may be operably coupled to the element 610 and configured to provide a current to the element 610 responsive to receiving operating instructions from the one or more processors 602. In some embodiments, the one or more driver circuits 606 comprise a closed-loop controller configured for modulating a temperature of the element 610. The closed-loop controller may be configured to control a temperature of a resistive heater of the microhotplate, such as by driving the element 610. In other embodiments, the closed-loop controller may be configured to control a temperature of interdigitated electrodes of the microhotplate, such as by driving the element 610. In some embodiments, the one or more driver circuits 606 may comprise a digital-to-analog converter.

The element 610 may be configured to receive a current from the one or more driver circuits 606. Wherein the element 610 comprises a resistive heater, the resistive heater may be substantially similar to the resistive heaters described above with respect to the devices 100, 200, 300, 300', 400. The one or more sensors 608 may be configured to sense at least one property of the element 610. By way of non-limiting example, the one or more sensors 608 may be configured to sense a voltage drop across the element 610. In other embodiments, the one or more sensors 608 may comprise an interdigitated electrode, such as the interdigitated electrodes described above with respect to the devices 100, 200, 300, 300', 400 and may be configured to determine a resistivity between the interdigitated electrodes. The one or more sensors 608 may comprise an analog-to-digital converter.

The one or more processors 602 may be configured to receive data from one or more sensors 608 and determine one or more properties of a material (e.g., gas, vapor, liquid, or solid) being analyzed. The one or more processors 602 may comprise a circuit, a controller, or both and may be configured to receive a sensed voltage from the one or more sensors 608 and may be configured to determine one or more of a power, a resistance, and a temperature of one or more microhotplates to determine a composition of an analyte based, at least in part, on a provided current from the one or more driver circuits 606 and as described above with reference to Equations (1) through (7). In some embodiments, the one or more processors 602 may be configured to determine an analyte (e.g., a presence thereof, a concentration thereof, etc.) in contact with a coating material of a microhotplate based, at least in part, on a voltage measured across sense lines, as described above with reference to FIG. 4A and FIG. 4B. In some embodiments, the one or more processors 602 may be configured to determine an analyte in contact with a chemical sensing material by measuring a resistance of interdigitated electrodes, as described above with reference to FIG. 1B, FIG. 3A, and FIG. 3B, for example.

The memory device 604 may be used to hold computing instructions, data, and other information for performing a wide variety of tasks including performing embodiments of the present disclosure. In some embodiments, the baseline data from previous temperature ramps (e.g., power versus temperature data), as described above with reference to Equations (4) through (7), may be stored in the memory. The processor 602 may be configured to subtract current data from previous data to produce a signal representing changes in microhotplate catalytic thermal response (Delta Cat) with respect to temperature. By way of example, and not limitation, the memory device 604 may include Synchronous Random Access Memory (SRAM), Dynamic RAM (DRAM), Read-Only Memory (ROM), Flash memory, phase change memory, and other suitable information storage devices. The memory device 604 may include data related to the device, including operating parameters (e.g., a temperature of the microhotplate, a composition of the microhotplate, etc.). The memory device 604 may include data relating to the microhotplate, the composition of the microhotplate, the temperature of the microhotplate, the resistance of the microhotplate, and a voltage of a resistive heater associated with the microhotplate.

Figure 7:
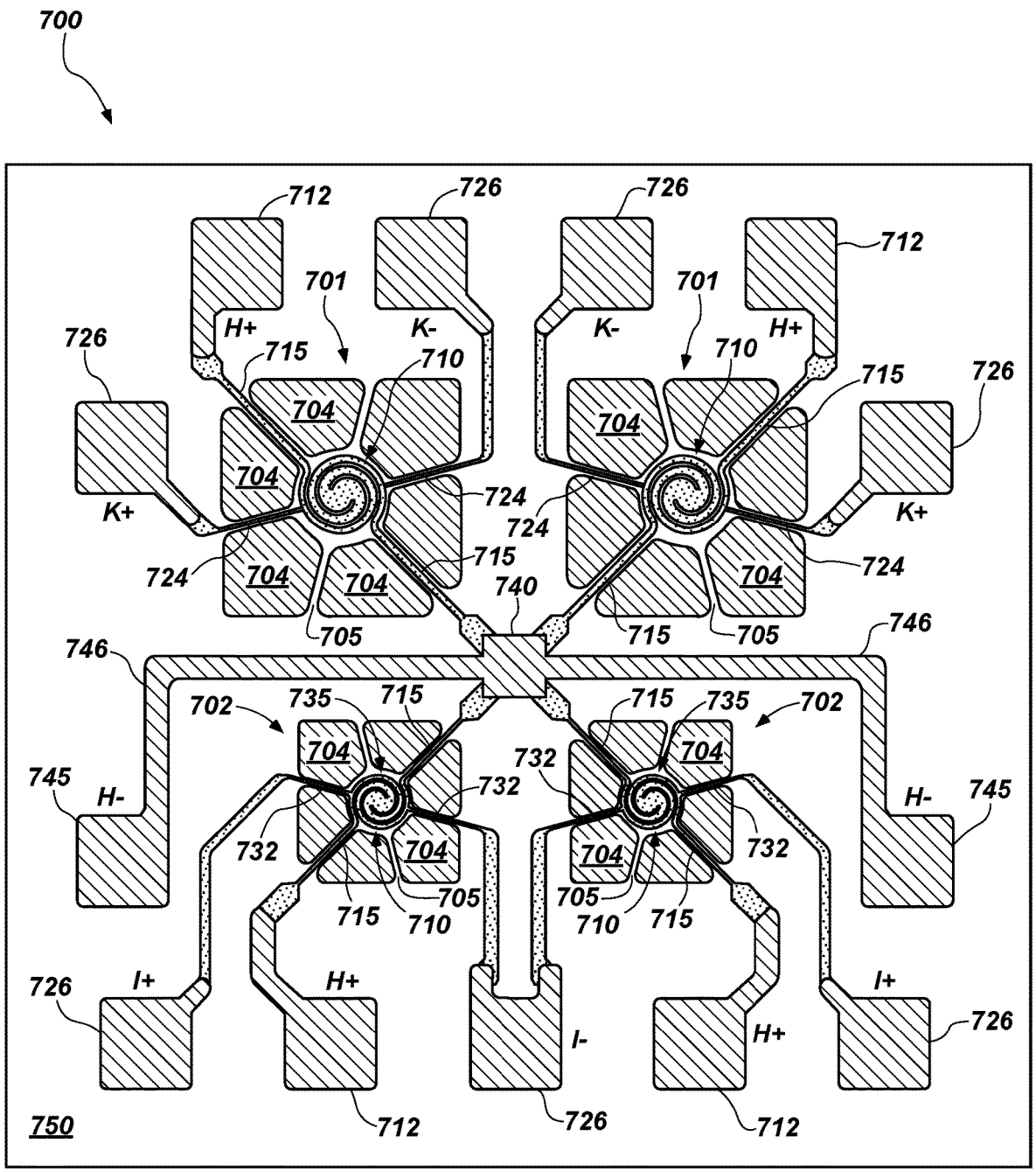
FIG. 7 is a plan view of a device including at least one microhotplate, in accordance with embodiments of the disclosure.

FIG. 7 is a plan view of a system 700 (e.g., a sensor) showing the layout of a plurality of devices, each including a microhotplate. The system 700 may comprise an array of microhotplate devices and may include at least some devices 701 that do not include interdigitated electrodes and at least some devices 702 that include interdigitated electrodes 735 over a resistive heater 710. The array may be referred to herein as a multi-sensor array, since it includes a plurality of sensors. In some embodiments, the devices 701 that do not include interdigitated electrodes may comprise a reference microhotplate or a catalytic microhotplate and the devices that include the interdigitated electrodes 735 may comprise a MOS microhotplate. In some embodiments, the system 700 includes at least one reference microhotplate device, at least one catalytic microhotplate device, and at least one MOS microhotplate device.

The devices 701, 702 may each include a void 704 formed in a substrate 750. The devices 701, 702 may further include a plurality of tethers 705 extending from the substrate 750 at from a periphery of the devices 701, 702 to a center portion thereof, as described in FIG. 1A through FIG. 4B.

The devices 701 that do not include the interdigitated electrodes 735 may have a diameter of about 100 μm, which may be about twice as large as a diameter of the devices 702 that include the interdigitated electrodes 735. In some embodiments, the devices 702 have a diameter of about 50

µm. In some embodiments, the devices 701 may include a catalyst material (e.g., such as the coating material 402 described above with reference to FIG. 4A and FIG. 4B) and may be relatively larger than the devices 702. In some embodiments, the larger size of the devices 701 may facilitate a more sensitive sensor device, since changes in power to maintain a predetermined temperature may be measured with a greater sensitivity. In some embodiments, at least one of the devices 701 comprises a catalyst material and at least another of the devices 701 comprises an inert material having at least one of a similar mass, thermal mass, or other property as the catalyst material of the other at least one device 701. In some embodiments, at least one of the devices 701 comprises a catalyst material and at least another of the devices 701 comprises no coating material.

The devices 701 may include sense lines 724 that are electrically coupled to each of the resistive heater 710 and sense line bond pads 726. The sense lines 724 may be configured to measure a voltage drop across the resistive heaters 710, as described above with reference to FIG. 1A through FIG. 1F. In some embodiments, the sense lines 724 may comprise Kelvin sense lines (i.e., four-terminal sensing, with two terminals comprising a bond pad 712, a common power source 740, and the two sense line bond pads 726).

Each device 701, 702 may include bond pads 712 coupled to electrically conductive traces 715, which, in turn, may be coupled to a resistive heater 710. In some embodiments, the devices 702 are substantially similar to the devices 100, 200, 300, 300' described above with reference to FIG. 1A through FIG. 3B. The devices 702 may further include interdigitated electrodes 735 at the center thereof and overlying respective resistive heaters 710 thereof, as described above with reference to, for example, FIG. 1B. A chemical sensing material may overlie and be in direct contact with the interdigitated electrodes 735, as described above with reference to, for example, FIG. 1C, FIG. 1D, and FIG. 1E. The interdigitated electrodes 735 may be in electrical contact with electrode traces 732 that, in turn, may be in electrical contact with bond pads 726.

The resistive heater 710 of each device 701, 702 may be in electrical contact with the common power source 740. By way of non-limiting example, bond pads 745 may be in electrical contact with conductive lines 746, which may be in electrical contact with one conductive trace 715 of each device 701, 702. In some such embodiments, each device 701, 702 may be electrically coupled to a common power source. The common power source 740 may include a metallization layer (e.g., a bond pad) configured to electrically couple each of the bond pads 745.

In some embodiments, each of the common power source 740, the bond pads 745, the bond pads 712, the sense line bond pads 726, the bond pads 730, and the conductive lines 746 may comprise the same material, such as, for example, gold. In some embodiments, each of the common power source 740, the bond pads 745, the bond pads 712, the sense line bond pads 726, the bond pads 730, and the conductive lines 746 may comprise a different material (e.g., such as a material exhibiting a relatively lower electrical resistance) than the electrically conductive traces 715, the sense lines 724, the resistive heaters 710, or the interdigitated electrodes 735, which may comprise, for example, tungsten, palladium, or other materials, as described above.

Accordingly, an array may comprise any combination of catalytic microhotplates, reference microhotplates, and metal oxide semiconductor (MOS) microhotplates of varying sizes and coatings. One or more reference microhotplates may be used to determine a thermal conductivity of an analyte, one or more catalytic microhotplates may be used to determine one or more ignition temperatures of one or more species in an analyte, an exothermic event, and an endothermic event of an analyte, and one or more MOS microhotplates may be used to determine an electrical response of a chemical sensing material at different temperatures to determine a presence of one or more species (e.g., analytes) in the sample. In some embodiments, the use of each microhotplate device may provide for orthogonal detection of one or more species in the analyte and may be used to analyze, differentiate, and quantify a plurality of chemical species. In some embodiments, flame arrestors or filters may be included over some or all of the microhotplate devices 701, 702.

In some embodiments, the interdigitated electrodes 735 of at least some of the devices 702 may be different (have a different size, shape, different composition, etc.) than the interdigitated electrodes 735 of other of the devices 702. In some embodiments, gaps between interdigitated electrodes 735 (such as between a first electrode and a second electrode comprising the interdigitated electrodes 735) may be different.

In some embodiments, the system 700 may include a plurality of devices 701 and devices 702 to facilitate additional analysis of a sample and/or analyte. For example, the system 700 may include a plurality of devices 701 including, for example, devices 701 comprising an inert coating material and devices 701 comprising a catalytic coating material, as described above with reference to FIG. 4A and FIG. 4B. The devices 701 may be used to determine, for example, a thermal conductivity of a sample and/or analyte, an exothermic reaction, an endothermic reaction, a temperature of an exothermic reaction, a temperature of an endothermic reaction, another property, or combinations thereof. The system 700 may further include devices 702 including interdigitated electrodes 735 and configured to measure a temperature of interaction between at least one analyte and a metal oxide semiconductor coating material of the devices 702.

The devices 100, 200, 300, 300' described above may be configured to reduce heat losses from the membrane 101 to the underlying substrate 102 through the tethers 105, 105a, 105b. In addition, the resistive heater 110 may be shaped and configured to reduce radiative heat losses therefrom to the surrounding environment. In some embodiments, heat transferred from the membrane 101 to the environment proximate the membrane 101 may be increased, which may facilitate determining one or more properties of an analyte proximate the membrane 101.

Additional non-limiting example embodiments of the disclosure are set forth below:

Embodiment 1: A microhotplate, comprising: a membrane suspended over a substrate by a plurality of tethers connected between the substrate and the membrane, the membrane comprising: a resistive heater comprising an electrically conductive material having a varying width from a peripheral portion of the membrane to a center of the membrane, the electrically conductive material comprising: a first portion spiraling in a first direction; and a second portion spiraling in a second direction and in electrical contact with the first portion proximate the center of the membrane; and a first electrically conductive trace extending over a first tether and in electrical contact with a bond pad on the substrate and the first portion and a second electrically conductive trace extending over another tether and in electrical contact with another bond pad on the substrate and the second portion.

Embodiment 2: The microhotplate of Embodiment 1, wherein the membrane comprises two or more dielectric materials, the resistive heater disposed between the two or more dielectric materials; and each tether of the plurality of tethers comprises the two or more dielectric materials, at least one tether of the plurality of tethers comprising an electrically conductive trace.

Embodiment 3: The microhotplate of Embodiment 1 or Embodiment 2, wherein the membrane further comprises at least one of a chemical sensing material, a catalytic coating material, and an inert coating material.

Embodiment 4: The microhotplate of any one of Embodiments 1 through 3, wherein the membrane comprises at least one material selected from the group consisting of silicon, a silicon oxide, a silicon nitride material, a silicon carbide, or a silicon oxynitride.

Embodiment 5: The microhotplate of any one of Embodiments 1 through 4, wherein the resistive heater is disposed between two or more dielectric materials, each dielectric material of the two or more dielectric materials comprising silicon nitrides, silicon oxides, silicon carbides, oxynitrides, or combinations thereof.

Embodiment 6: The microhotplate of Embodiment 5, wherein the two or more dielectric materials exhibit different residual stresses.

Embodiment 7: The microhotplate of Embodiment 5 or Embodiment 6, wherein at least one dielectric material of the two or more dielectric materials exhibits a residual tensile stress of between about 200 MPa and about 2.0 GPa at about 20° C.

Embodiment 8: The microhotplate of any one of Embodiments 5 through 7, wherein the two or more dielectric materials are selected to exhibit a reduced residual tensile stress at operating temperatures of the microhotplate.

Embodiment 9: The microhotplate of any one of Embodiments 5 through 8, wherein the two or more dielectric materials s are in tension between a temperature between 600° C. and about 1,200° C.

Embodiment 10: The microhotplate of any one of Embodiments 1 through 9, wherein the second portion is disposed at least between adjacent spirals of the first portion.

Embodiment 11: The microhotplate of any one of Embodiments 1 through 10, wherein a gap between the first portion and the second portion is substantially constant and smaller than a minimum width of the electrically conductive material.

Embodiment 12: The microhotplate of any one of Embodiments 1 through 11, wherein the membrane has a polygonal shape.

Embodiment 13: The microhotplate of any one of Embodiments 1 through 12, further comprising an electrically conductive sense line trace in electrical contact with the first portion and an electrically conductive sense line trace in electrical contact with the second portion, the electrically conductive sense line traces configured to measure a voltage across the resistive heater.

Embodiment 14: The microhotplate of any one of Embodiments 1 through 13, wherein the resistive heater comprises a widened curved portion at an intersection of at least one tether and the membrane.

Embodiment 15: The microhotplate of any one of Embodiments 1 through 14, wherein the resistive heater comprises an increasing width from the widened portion to the center of the membrane.

Embodiment 16: The microhotplate of any one of Embodiments 1 through 15, wherein each tether of the plurality of tethers has a greater width proximate the membrane and the substrate than at portions distal from the membrane and the substrate.

Embodiment 17: The microhotplate of any one of Embodiments 1 through 16, wherein each tether of the plurality of tethers comprises a fillet shape or a double tangent arc shape proximate the membrane and the substrate.

Embodiment 18: The microhotplate of any one of Embodiments 1 through 17, wherein outer edges of the electrically conductive material are substantially free of corners and comprise arcuate surfaces.

Embodiment 19: The microhotplate of any one of Embodiments 1 through 18, further comprising a chemical sensitive material over a dielectric material overlying the resistive heater.

Embodiment 20: The microhotplate of Embodiment 19, further comprising a plurality of electrodes in electrical contact with the chemical sensitive coating material and configured to measure a resistivity of the chemical sensitive coating material.

Embodiment 21: The microhotplate of Embodiment 20, wherein the plurality of electrodes comprises a plurality of interdigitated electrodes, a plurality of interdigitated spiral electrodes, or a plurality of interdigitated concentric electrodes.

Embodiment 22: The microhotplate of any one of Embodiments 1 through 21, further comprising one of a catalytic coating material and one of an inert coating material or no coating material over resistive heater.

Embodiment 23: A chemical sensor comprising at least one microhotplate, the at least one microhotplate comprising: a plurality of tethers extending over a void formed in a substrate, the plurality of tethers supporting a membrane over the substrate and comprising a plurality of dielectric layers, the membrane comprising: a resistive heater between two dielectric layers of the plurality of dielectric layers, the resistive heater comprising an electrically conductive material having a first portion spiraling in a first direction and a second portion spiraling in a second, opposite direction, the electrically conductive material having a varying width from an outer portion of the resistive heater to a central portion thereof; and electrically conductive heater traces configured to provide power to the resistive heater, the electrically conductive heater traces overlying at least one of the tethers.

Embodiment 24: The chemical sensor of Embodiment 23, wherein the plurality of tethers comprise six tethers, the electrically conductive heater traces overlying two of the tethers, electrically conductive sense line traces overlying two of the tethers in electrical communication with the resistive heater, and chemical sensing electrode traces overlying two of the tethers and in electrical communication with interdigitated electrodes overlying the resistive heater.

Embodiment 25: The chemical sensor of Embodiment 23 or Embodiment 24, further comprising electrically conductive sense line traces in electrical contact with the resistive heater and configured to measure a voltage across the resistive heater.

Embodiment 26: The chemical sensor of Embodiment 25, further comprising a controller configured to determine a temperature of the resistive heater at least by dividing a voltage measured by the electrically conductive sense line traces by a current provided to the resistive heater.

Embodiment 27: The chemical sensor of any one of Embodiments 23 through 26, further comprising a controller configured to control a temperature of the resistive heater.

Embodiment 28: The chemical sensor of any one of Embodiments 23 through 27, wherein the resistive heater comprises tungsten, platinum, molybdenum, tantalum, titanium tungsten, alloys thereof, and multilayer structures thereof.

Embodiment 29: The chemical sensor of any one of Embodiments 23 through 28, further comprising a controller configured to determine a temperature of the resistive heater based, at least in part, on a current supplied to the resistive heater.

Embodiment 30: The chemical sensor of any one of Embodiments 23 through 29, wherein each tether of the at least five tethers is wider proximate the membrane and proximate the substrate than at other portions of the tether.

Embodiment 31: The chemical sensor of any one of Embodiments 23 through 30, wherein the substrate comprises at least one of silicon, silicon dioxide, and silicon nitride.

Embodiment 32: A method of measuring at least one of a thermal conductivity, an exothermic event, and an endothermic event, the method comprising: providing a current to a resistive heater of at least one microhotplate, the resistive heater comprising a varying width from a peripheral portion thereof toward a center thereof, the resistive heater comprising a first portion extending from the peripheral portion toward the center thereof and spiraling in a clockwise direction and a second portion in contact with the first portion at the center of the resistive heater and extending from the center of the resistive heater toward the peripheral portion thereof and spiraling in a counterclockwise direction; and measuring a voltage across the resistive heater; and calculating a resistance of the resistive heater to determine an average temperature of the resistive heater.

Embodiment 33: The method of Embodiment 32, further comprising determining a resistivity of a chemical sensing material disposed over the resistive heater.

Embodiment 34: The method of Embodiment 33, wherein determining a resistivity of a chemical sensing material comprises measuring the resistivity between interdigitated electrodes in contact with the chemical sensing material.

Embodiment 35: The method of any one of Embodiments 32 through 34, wherein measuring a voltage across the resistive heater comprises measuring the voltage across the resistive heater with sense lines coupled to the resistive heater.

Embodiment 36: The method of any one of Embodiments 32 through 35, wherein calculating a resistance of the resistive heater comprises calculating the resistance of the resistive heater based, at least in part, on the voltage measured across the resistive heater.

Embodiment 37: The method of any one of Embodiments 32 through 36, wherein determining an average temperature of the resistive heater comprises determining the average temperature of the resistive heater based, at least in part, on the resistance of the resistive heater and a temperature coefficient of resistance of the resistive heater.

Embodiment 38: The method of any one of Embodiments 32 through 37, further comprising determining a power supplied to the resistive heater based, at least in part, on the voltage measured across the resistive heater and the provided current.

Embodiment 39: The method of any one of Embodiments 32 through 38, further comprising determining a power required to maintain a temperature of a catalytic material over the resistive heater.

Embodiment 40: A sensor for providing orthogonal analysis of a sample, the sensor comprising: an array of microhotplates, at least one microhotplate of the array of microhotplates comprising a resistive heater comprising an electrically conductive material having a varying width from a peripheral portion of the membrane to a center of the membrane, the electrically conductive material comprising: a first portion spiraling in a first direction; and a second portion spiraling in a second direction and in electrical contact with the first portion proximate the center of the membrane; and a controller configured to determine one or more of at least one property of the resistive heater of at least one microhotplate of the array of microhotplates and a resistance between interdigitated electrodes of at least one microhotplate of the array of microhotplates.

Embodiment 41: The sensor of Embodiment 40, wherein at least one microhotplate of the array of microhotplates comprises a catalytic coating over a dielectric material overlying the resistive heater.

Embodiment 42: The sensor of Embodiment 40 or Embodiment 41, wherein at least one microhotplate of the array of microhotplates comprises an inert coating material or no coating material over a dielectric material overlying the resistive heater.

Embodiment 43: The sensor of any one of Embodiments 40 through 42, wherein at least one microhotplate of the array of microhotplates comprises an n-type semiconductor material.

Embodiment 44: The sensor of any one of Embodiments 40 through 43, wherein at least one microhotplate of the array of microhotplates comprises a p-type semiconductor material.

Embodiment 45: The sensor of any one of Embodiments 40 through 44, wherein at least one microhotplate of the array of microhotplates comprises an ionic conductor.

Embodiment 46: The sensor of any one of Embodiments 40 through 45, wherein the array of microhotplates comprises: at least one reference microhotplate comprising an inert material overlying a dielectric material over its resistive heater or free of a coating material; at least one microhotplate comprising a catalytic coating over a dielectric material of its resistive heater; and at least one microhotplate comprising a chemical sensing material selected from the group consisting of a p-type semiconductor, an n-type semiconductor, and an ionic conductor overlying a dielectric material over its resistive heater.

Embodiment 47: The sensor of any one of Embodiments 40 through 46, further comprising at least one filter configured to filter one or more materials from the sample.

Embodiment 48: The sensor of any one of Embodiments 40 through 47, wherein the resistive heater is configured to operate at a temperature between about 200° C. and about 1,200° C.

Embodiment 49: A method of measuring a response from a sensor comprising an array of microhotplates, the method comprising: providing a current to a resistive heater of each microhotplate of an array of microhotplates, the resistive heater of each microhotplate having a varying width from a peripheral portion of the membrane to a center of the membrane, the electrically conductive material comprising: a first portion spiraling in a first direction; and a second portion spiraling in a second direction and in electrical contact with the first portion proximate the center of the membrane; and measuring a response from each microhotplate of the array of microhotplates, wherein measuring a response from each microhotplate of the array of microhotplates comprises: analyzing a response from at least one reference microhotplate free of a coating material or comprising an inert material overlying a dielectric material over its resistive heater; analyzing a response from at least one microhotplate comprising a catalytic material overlying a dielectric material over its resistive heater; and analyzing a response from at least one microhotplate comprising a chemical sensing material selected from the group consisting of a p-type semiconductor, an n-type semiconductor, and an ionic conductor overlying a dielectric material over its resistive heater.

Embodiment 50: The method of Embodiment 49, wherein analyzing a response from at least one microhotplate comprising a catalytic material overlying a dielectric material over its resistive heater comprises determining a difference between the response from the at least one microhotplate comprising the catalytic material and the response from the at least one reference microhotplate.

Embodiment 51: The method of Embodiment 49 or Embodiment 50, wherein analyzing a response from at least one reference microhotplate comprises maintaining a temperature of the at least one reference microhotplate and determining a power required to maintain the temperature of the at least one reference microhotplate.

Embodiment 52: The method of any one of Embodiments 49 through 51, wherein analyzing a response from at least one reference microhotplate comprises maintaining a current provided to the resistive heater of the at least one reference microhotplate and measuring a change in temperature of the resistive heater of the at least one reference microhotplate.

Embodiment 53: A sensor for analyzing a sample, the sensor comprising: a microhotplate comprising a membrane suspended over a substrate by a plurality of tethers connected between the substrate and the membrane, the membrane comprising: a resistive heater comprising an electrically conductive material having a varying width from a peripheral portion of the membrane to a center of the membrane, the electrically conductive material comprising: a first portion spiraling in a first direction; and a second portion spiraling in a second direction and in electrical contact with the first portion proximate the center of the membrane; and a first electrically conductive trace extending over a first tether and in electrical contact with a bond pad on the substrate and the first portion and a second electrically conductive trace extending over another tether and in electrical contact with another bond pad on the substrate and the second portion.

Embodiment 54: The sensor of Embodiment 53, wherein: the membrane comprises two or more dielectric materials, the resistive heater disposed between the two or more dielectric materials; and each tether of the plurality of tethers comprises the two or more dielectric materials, at least one tether of the plurality of tethers comprising an electrically conductive trace.

Embodiment 55: The sensor of Embodiment 53 or Embodiment 54, wherein the membrane further comprises at least one of a chemical sensing material, a catalytic coating material, and an inert coating material.

Embodiment 56: The sensor of any one of Embodiments 53 through 55, wherein the second portion is disposed at least between adjacent spirals of the first portion.

Embodiment 57: The sensor of any one of Embodiments 53 through 56, wherein a gap between the first portion and the second portion is substantially constant and smaller than a minimum width of the electrically conductive material.

Embodiment 58: The sensor of any one of Embodiments 53 through 57, wherein the membrane has a polygonal shape.

Embodiment 59: The sensor of any one of Embodiments 53 through 58, further comprising a first electrically conductive sense line trace in electrical contact with the first portion and a second electrically conductive sense line trace in electrical contact with the second portion, the first electrically conductive sense line trace and the second electrically conductive sense line trace configured to measure a voltage across the resistive heater.

Embodiment 60: The sensor of Embodiment 59, wherein the first electrically conductive sense line trace is in electrical contact with the first portion at a location that is not located between the first portion and the second portion.

Embodiment 61: The sensor of any one of Embodiments 53 through 60, wherein the resistive heater comprises a widened curved portion at an intersection of at least one tether and the membrane.

Embodiment 62: The sensor of any one of Embodiments 53 through 61, wherein the resistive heater comprises a continuously increasing width from the widened portion to the center of the membrane.

Embodiment 63: The sensor of any one of Embodiments 53 through 62, wherein each tether of the plurality of tethers has a greater width proximate the membrane and the substrate than at portions distal from the membrane and the substrate.

Embodiment 64: The sensor of any one of Embodiments 53 through 63, further comprising a plurality of electrodes in electrical contact with a chemical sensitive coating material overlying the resistive heater, the plurality of electrodes comprising interdigitated electrodes and configured to measure a resistivity of the chemical sensitive coating material.

Embodiment 65: The sensor of any one of Embodiments 53 through 64, wherein the plurality of tethers connected between the substrate and the membrane comprises at least two tethers.

Embodiment 66: The sensor of any one of Embodiments 53 through 65, wherein the plurality of tethers comprises six tethers, the first electrically conductive trace and the second electrically conductive trace overlying two of the tethers, electrically conductive sense line traces overlying two of the tethers in electrical communication with the resistive heater, and chemical sensing electrode traces overlying two of the tethers and in electrical communication with interdigitated electrodes overlying the resistive heater.

Embodiment 67: The sensor of any one of Embodiments 53 through 66, further comprising a controller configured to determine a resistance, which is proportional to temperature, of the resistive heater at least by dividing a voltage measured by the first electrically conductive sense line trace and the second electrically conductive sense line trace by a current provided to the resistive heater.

Embodiment 68: The sensor of any one of Embodiments 53 through 67, further comprising: an array of microhotplates; and a controller configured to determine one or more of at least one property of the resistive heater of at least one microhotplate of the array of microhotplates and a resistance between interdigitated electrodes of at least one microhotplate of the array of microhotplates.

Embodiment 69: The sensor of Embodiment 68, wherein the array of microhotplates comprises: at least one reference microhotplate comprising an inert material overlying a dielectric material over its resistive heater or free of a coating material; at least one microhotplate comprising a catalytic coating over a dielectric material of its resistive heater; and at least one microhotplate comprising a chemical sensing material selected from the group consisting of a p-type semiconductor, an n-type semiconductor, and an ionic conductor overlying a dielectric material over its resistive heater.

Embodiment 70: A method of measuring at least one of a thermal conductivity, an exothermic event, an endothermic event, and a presence of one or more chemicals in a sample, the method comprising: providing a current to a resistive heater of at least one microhotplate of a multi-sensor array, the resistive heater comprising a varying width from a peripheral portion thereof toward a center thereof, the resistive heater comprising a first portion extending from the peripheral portion toward the center thereof and spiraling in a clockwise direction and a second portion in contact with the first portion at the center of the resistive heater and extending from the center of the resistive heater toward the peripheral portion thereof and spiraling in a counterclockwise direction; measuring a voltage across the resistive heater; calculating a resistance of the resistive heater based at least on the measured voltage across the resistive heater and the current provided to the resistive heater; determining a temperature of the resistive heater based on the resistance of the resistive heater; and determining a power required to maintain a given temperature to determine a thermal conductivity, an endothermic event, an exothermic event, or a presence of one or more chemicals of the sample.

Embodiment 71: The method of Embodiment 70, wherein measuring a voltage across the resistive heater comprises measuring the voltage across the resistive heater with sense lines coupled to the resistive heater.

Embodiment 72: The method of Embodiment 70 or Embodiment 71, further comprising determining a power supplied to the resistive heater based, at least in part, on the voltage measured across the resistive heater and the provided current.

Embodiment 73: The method of any one of Embodiments 70 through 72, further comprising: providing an electrical current to a resistive heater of at least one metal oxide semiconductor microhotplate comprising a chemical sensing material selected from the group consisting of a p-type semiconductor, an n-type semiconductor, and an ionic conductor overlying sense electrodes overlying a dielectric material over the resistive heater of the at least one metal oxide semiconductor microhotplate; and measuring a response of the at least one metal oxide semiconductor microhotplate.

Embodiment 74: The method of Embodiment 73, further comprising determining a resistivity of a chemical sensing material disposed over an interdigitated electrode disposed over the resistive heater of the at least one metal oxide semiconductor microhotplate.

Embodiment 75: The method of any one of Embodiments 70 through 74, wherein measuring a response of the at least one microhotplate comprises: measuring a response of at least one microhotplate comprising a catalytic material overlying a dielectric material over its resistive heater; measuring a response of a reference microhotplate; and determining a difference between the response of the at least one microhotplate comprising the catalytic material and the response of the reference microhotplate.

Embodiment 76: The method of any one of Embodiments 70 through 75, wherein calculating a resistance of the resistive heater comprises compensating the measured voltage by subtracting a voltage drop across electrically conductive traces and a heater interconnect structure in electrical communication with the resistive heater.

While the disclosure is susceptible to various modifications and alternative forms, specific embodiments have been shown by way of example in the drawings and have been described in detail herein. However, the disclosure is not intended to be limited to the particular forms disclosed. Rather, the disclosure is to cover all modifications, equivalents, and alternatives falling within the scope of the disclosure as defined by the following appended claims and their legal equivalents.

What is claimed is:

1. A sensor for analyzing a sample, the sensor comprising:
a microhotplate comprising a membrane suspended over a substrate by a plurality of tethers connected between the substrate and the membrane, the membrane comprising:
a resistive heater comprising an electrically conductive material, a width of the electrically conductive material continuously decreasing from a center of the membrane to a peripheral portion of the membrane, the electrically conductive material comprising:
a first portion spiraling in a first direction; and
a second portion spiraling in a second direction and in electrical contact with the first portion proximate the center of the membrane;
a first electrically conductive trace extending over a first tether and in electrical contact with a bond pad on the substrate and the first portion; and
a second electrically conductive trace extending over a second tether and in electrical contact with another bond pad on the substrate and the second portion.

2. The sensor of claim 1, wherein:
the resistive heater overlies a first dielectric material and a second dielectric material, a third dielectric material overlying the resistive heater; and
the first tether and the second tether each comprise the first dielectric material, the second dielectric material, and the third dielectric material.

3. The sensor of claim 2, wherein the membrane further comprises at least one of a chemical sensing material, a catalytic coating material, and an inert coating material.

4. The sensor of claim 1, wherein the second portion is disposed at least between adjacent spirals of the first portion.

5. The sensor of claim 1, wherein a gap between the first portion and the second portion is substantially constant and smaller than a minimum width of the electrically conductive material.

6. The sensor of claim 1, wherein the membrane has a polygonal shape.

7. The sensor of claim 1, further comprising:
a first electrically conductive sense line trace in electrical contact with the first portion and extending over a third tether; and
a second electrically conductive sense line trace in electrical contact with the second portion and extending over a fourth tether, the first electrically conductive sense line trace and the second electrically conductive sense line trace configured to measure a voltage across the resistive heater.

8. The sensor of claim 7, wherein the first electrically conductive sense line trace is in electrical contact with the first portion at a location that is not located between the first portion and the second portion.

9. The sensor of claim 1, wherein the resistive heater comprises a widened curved portion at an intersection of at least one tether and the membrane.

10. The sensor of claim 1, wherein the width of the heater decreases with an increasing radial distance from the center of the membrane.

11. The sensor of claim 1, wherein each tether of the plurality of tethers has a greater width proximate the membrane and the substrate than at portions distal from the membrane and the substrate.

12. The sensor of claim 11, further comprising a plurality of electrodes in electrical contact with a chemical sensitive coating material overlying the resistive heater, the plurality of electrodes comprising interdigitated electrodes and configured to measure a resistivity of the chemical sensitive coating material.

13. The sensor of claim 1, wherein the plurality of tethers connected between the substrate and the membrane comprises at least three tethers.

14. The sensor of claim 13, wherein the plurality of tethers comprises six tethers, the first electrically conductive trace and the second electrically conductive trace overlying two of the tethers, electrically conductive sense line traces overlying two of the tethers in electrical communication with the resistive heater, and chemical sensing electrode traces overlying two of the tethers and in electrical communication with interdigitated electrodes overlying the resistive heater.

15. The sensor of claim 14, further comprising a controller configured to determine a resistance of the resistive heater at least by dividing a voltage measured by the first electrically conductive sense line trace and the second electrically conductive sense line trace by a current provided to the resistive heater.

16. The sensor of claim 1, further comprising:
an array of microhotplates; and
a controller configured to determine one or more of at least one property of the resistive heater of at least one microhotplate of the array of microhotplates and a resistance between interdigitated electrodes of at least one microhotplate of the array of microhotplates.

17. The sensor of claim 16, wherein the array of microhotplates comprises:
at least one reference microhotplate comprising an inert material overlying a dielectric material over a resistive heater of the at least one reference microhotplate or free of a coating material;
at least one microhotplate comprising a catalytic coating over a dielectric material of a resistive heater of the at least one microhotplate comprising the catalytic coating; and
at least one microhotplate comprising a chemical sensing material selected from the group consisting of a p-type semiconductor, an n-type semiconductor, and an ionic conductor overlying a dielectric material over a resistive heater of the at least one microhotplate comprising the chemical sensing material.

18. A method of measuring at least one of a thermal conductivity, an exothermic event, an endothermic event, and a presence of one or more chemicals in a sample, the method comprising:
providing a current to a resistive heater of at least one microhotplate of a multi-sensor array, the at least one microhotplate comprising a membrane suspended over a substrate by a plurality of tethers connected between the substrate and the membrane, the membrane comprising the resistive heater, the resistive heater comprising an electrically conductive material, a width of the electrically conductive material continuously decreasing from a center of the membrane to a peripheral portion of the membrane, the resistive heater comprising a first portion extending from the peripheral portion toward the center thereof and spiraling in a clockwise direction and a second portion in contact with the first portion at the center of the resistive heater and extending from the center of the resistive heater toward the peripheral portion thereof and spiraling in a counterclockwise direction, wherein providing the current to the resistive heater comprises providing the current between a first electrically conductive trace extending over a first tether and in electrical contact with a bond pad on the substrate and the first portion and a second electrically conductive trace extending over a second tether and in electrical contact with another bond pad on the substrate and the second portion;
measuring a voltage across the resistive heater;
calculating a resistance of the resistive heater based at least on the measured voltage across the resistive heater and the current provided to the resistive heater;
determining a temperature of the resistive heater based on the resistance of the resistive heater; and
determining a power required to maintain a given temperature to determine a thermal conductivity, an endothermic event, an exothermic event, or a presence of one or more chemicals of the sample.

19. The method of claim 18, wherein measuring a voltage across the resistive heater comprises measuring the voltage across the resistive heater with sense lines coupled to the resistive heater.

20. The method of claim 18, further comprising determining a power supplied to the resistive heater based, at least in part, on the voltage measured across the resistive heater and the provided current.

21. The method of claim 18, further comprising:
providing an electrical current to a resistive heater of at least one metal oxide semiconductor microhotplate comprising a chemical sensing material selected from the group consisting of a p-type semiconductor, an n-type semiconductor, and an ionic conductor overlying sense electrodes overlying a dielectric material over the resistive heater of the at least one metal oxide semiconductor microhotplate; and
measuring a response of the at least one metal oxide semiconductor microhotplate.

22. The method of claim 21, further comprising determining a resistivity of a chemical sensing material disposed over an interdigitated electrode disposed over the resistive heater of the at least one metal oxide semiconductor microhotplate.

23. The method of claim 18, wherein measuring a response of the at least one microhotplate comprises:
measuring a response of at least one microhotplate comprising a catalytic material overlying a dielectric material over its resistive heater;
measuring a response of a reference microhotplate; and
determining a difference between the response of the at least one microhotplate comprising the catalytic material and the response of the reference microhotplate.

24. The method of claim 18, wherein calculating a resistance of the resistive heater comprises compensating the measured voltage by subtracting a voltage drop across electrically conductive traces and a heater interconnect structure in electrical communication with the resistive heater.

* * * * *